(12) United States Patent
Merrill et al.

(10) Patent No.: US 10,766,896 B2
(45) Date of Patent: Sep. 8, 2020

(54) IMIDAZO[4,5-C] RING COMPOUNDS CONTAINING GUANIDINE SUBSTITUTED BENZAMIDE GROUPS

(71) Applicant: 3M INNOVATIVE PROPERTIES COMPANY, St. Paul, MN (US)

(72) Inventors: Bryon A. Merrill, River Falls, WI (US); George W. Griesgraber, Eagan, MN (US); Chad A. Haraldson, Apple Valley, MN (US); Kevin J. Bechtold, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/471,632

(22) PCT Filed: Feb. 27, 2018

(86) PCT No.: PCT/US2018/019922
§ 371 (c)(1),
(2) Date: Jun. 20, 2019

(87) PCT Pub. No.: WO2018/160552
PCT Pub. Date: Sep. 7, 2018

(65) Prior Publication Data
US 2020/0087298 A1    Mar. 19, 2020

Related U.S. Application Data

(60) Provisional application No. 62/465,347, filed on Mar. 1, 2017.

(51) Int. Cl.
C07D 471/04    (2006.01)
(52) U.S. Cl.
CPC ................. *C07D 471/04* (2013.01)
(58) Field of Classification Search
CPC ..................................................... C07D 471/04
See application file for complete search history.

(56) References Cited

U.S. PATENT DOCUMENTS

| | | |
|---|---|---|
| 4,689,338 A | 8/1987 | Gerster |
| 5,352,784 A | 10/1994 | Nikolaides |
| 5,446,153 A | 8/1995 | Lindstrom |
| 5,731,324 A | 3/1998 | Fisher |
| 5,773,646 A | 6/1998 | Chandrakumar |
| 5,876,756 A | 3/1999 | Takada |
| 6,039,969 A | 3/2000 | Tomai |
| 6,069,149 A | 5/2000 | Nanba |
| 6,110,929 A | 8/2000 | Gerster |
| 6,194,425 B1 | 2/2001 | Gerster |
| 6,200,592 B1 | 3/2001 | Tomai |
| 6,331,539 B1 | 12/2001 | Crooks |
| 6,451,810 B1 | 9/2002 | Coleman |
| 6,514,985 B1 * | 2/2003 | Gerster ............. A61P 37/00 514/293 |
| 6,573,273 B1 | 6/2003 | Crooks |
| 6,664,264 B2 | 12/2003 | Dellaria |
| 6,677,349 B1 | 1/2004 | Griesgraber |
| 6,784,188 B2 | 8/2004 | Crooks |
| 6,800,624 B2 | 10/2004 | Crooks |

(Continued)

FOREIGN PATENT DOCUMENTS

| | | |
|---|---|---|
| WO | WO 2000-76505 | 12/2000 |
| WO | WO 2005-051380 | 6/2005 |

(Continued)

OTHER PUBLICATIONS

Berge, "Pharmaceutical Salts", Journal of Pharmaceutical Sciences, 1977, vol. 66, No. 01, pp. 1-19.
Bernatowicz, "1 H-Pyrazole-a-carboxamidine Hydrochloride: An Attractive Reagent for Guanylation of Amines and Its Application to Peptide Synthesis", Journal of Organic Chemistry, 1992, vol. 57, No. 08, pp. 2497-2502.
Bernatowicz, "Urethane Protected Derivatives of 1-Guanylpyrazole for the Mild and Efficient Preparation of Guanidines", Tetrahedron Letters, 1993, vol. 34, No. 21, pp. 3389-3392.
Gennaro, "Remington's Pharmaceutical Sciences", 18$^{th}$ Edition, 1990, pp. 1-5.

(Continued)

*Primary Examiner* — Timothy R Rozof
(74) *Attorney, Agent, or Firm* — Eric E. Silverman

(57) ABSTRACT

Imidazo[4,5-c] ring compounds of formula I, (particularly imidazo4,5-c]quinolines, 6,7,8,9-tetrahydroimidazo[4,5-c] quinolines, imidazo[4,5-c]naphthyridines, and 6,7,8,9-tetrahydroimidazo[4,5-c]naphthyridine compounds) having a guanidine substituted benzamide that is attached at the N–1 position by a linking group, pharmaceutical compositions containing the compounds, and methods of making the compounds are disclosed. Methods of use of the compounds as immune response modifiers, for inducing cytokine biosynthesis in animals and in the treatment of diseases including viral and neoplastic diseases are also disclosed.

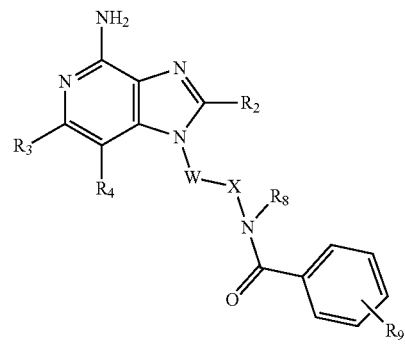

Formula I

24 Claims, No Drawings

(56) References Cited

U.S. PATENT DOCUMENTS

| | | |
|---|---|---|
| 6,888,000 B2 | 5/2005 | Crooks |
| 7,115,622 B2 | 10/2006 | Crooks |
| 7,163,947 B2 | 1/2007 | Griesgraber |
| 7,393,859 B2 | 7/2008 | Coleman |
| 7,544,697 B2 | 6/2009 | Hays |
| 7,579,359 B2 | 8/2009 | Krepski |
| 7,799,800 B2 | 9/2010 | Wightman |
| 7,884,207 B2 | 2/2011 | Stoermer |
| 7,915,281 B2 | 3/2011 | Moser |
| 7,968,563 B2 | 6/2011 | Kshirsagar |
| 8,088,790 B2 | 1/2012 | Kshirsagar |
| 8,168,802 B2 | 5/2012 | Hays |
| 8,673,932 B2 | 3/2014 | Kshirsagar |
| 8,691,837 B2 | 4/2014 | Krepski |
| 8,697,873 B2 | 4/2014 | Krepski |
| 8,728,486 B2 | 5/2014 | David |
| 9,034,336 B2 | 5/2015 | Ferguson |
| 2009/0005376 A1 | 1/2009 | Krepski |
| 2011/0269965 A1 | 11/2011 | Hays |
| 2013/0230578 A1 | 9/2013 | Wightman |

FOREIGN PATENT DOCUMENTS

| | | |
|---|---|---|
| WO | WO 2017-040233 | 3/2017 |
| WO | WO 2017-040234 | 3/2017 |

OTHER PUBLICATIONS

Greene, "Protective Groups in Organic Synthesis", Second Edition, 1991, John Wiley & Sons, pp. 1-4.

Higuchi, "Pro-drugs as Novel Drug Delivery Systems", American Chemical Society Symposium Series 14, 1975, pp. 1-4.

Katritzky, "Recent Developments in Guanylating Agents", ARKIVOC, 2005, pp. 49-87.

Kayser, "Modifications of the GSK3β Substrate Sequence to Produce Substrate-Mimetic Inhibitors of Akt As Potential Anti-Cancer Therapeutics", Bioorganic & Medicinal Chemistry Letters, 2007, vol. 17, pp. 2068-2073.

Kitamura, "Potent Dibasic GPIIb-IIIa Antagonists with Reduced Prolongation of Bleeding Time: Synthesis and Pharmacological Evaluation of 2-Oxopiperazine Derivatives", Journal of Medicinal Chemistry, 2001, vol. 44, No. 15, pp. 2438-2450.

Lee, "1H-Pyrazole-1-carboxamidines: New Inhibitors of Nitric Oxide Synthase", Biorganic & Medicinal Chemistry Letters, 2000, vol. 10, pp. 2771-2774.

Lee, "Solid-Phase Syntheses of $N^\omega$-Propylarginine-Containing Dipeptides, Dipeptide Esters, and Dipeptide Amides", Synthesis, 1999, No. SI, pp. 1495-1499.

Maryanoff, "A Convenient Synthesis of Guanidines from Thioureas", Journal of Organic Chemistry, 1986, vol. 51, pp. 1882-1884.

Roche, "Bioreverisble Carriers in Drug Design—Theory and Application", American Pharmaceutical Association, 1987, pp. 1-4.

Sagi, "Optimization of a Coagulation Factor VIIa Inhibitor Found in Factor Xa Inhibitor Library", Bioorganic & Medicinal Chemistry, 2005, vol. 13, pp. 1487-1496.

Shukla, "Structure-Activity Relationships in Human Toll-Like Receptor 7-Active Imidazoquinoline Analogues", Journal of Medicinal Chemistry, 2010, vol. 53, pp. 4450-4465, XP055081984.

Ueda, "Syntheses and Inhibitory Effects on Gastric Lesions of 4-Guanidinomethylbenzoic Acid Arylamides", Chemical and Pharmaceutical Bulletin, 1993, vol. 41, No. 08, pp. 1387-1390.

Zhang, "Recent Development of Synthetic Preparation Methods for Guanidines Via Transition Metal Catalysis", Chemical Communications, 2015, vol. 51, pp. 254-265.

International Search Report for PCT International Application No. PCT-US2018-019922, dated Apr. 26, 2018, 5 pages.

* cited by examiner

IMIDAZO[4,5-C] RING COMPOUNDS CONTAINING GUANIDINE SUBSTITUTED BENZAMIDE GROUPS

CROSS REFERENCE TO RELATED APPLICATIONS

This application is a national stage filing under 35 U.S.C. 371 of PCT/US2018/019922, filed Feb. 27, 2018, which claims the benefit of U.S. Provisional Application No. 62/465,347, filed Mar. 1, 2017, the disclosure of which is incorporated by reference in its/their entirety herein.

BACKGROUND

Some drug compounds act by stimulating certain key aspects of the immune system, as well as by suppressing certain other aspects (e.g., U.S. Pat. Nos. 6,039,969 and 6,200,592). These compounds are sometimes referred to as immune response modifiers (IRMs). Some IRM compounds are useful for treating viral diseases, neoplasias, and $T_H2$-mediated diseases; some are useful as vaccine adjuvants.

IRM compounds have been reported based on the following bicyclic and tricyclic ring systems: 1H-imidazo[4,5-c]quinolin-4-amines (e.g., U.S. Pat. No. 4,689,338); 1H-imidazo[4,5-c]pyridin-4-amines (e.g., U.S. Pat. No. 5,446,153); 1H-imidazo[4,5-c][1,5]naphthyidin-4-amines (e.g., U.S. Pat. No. 6,194,425); thiazolo[4,5-c]quinolone-4-amines and oxazolo[4,5-c]quinolone-4-amines (e.g., U.S. Pat. No. 6,110,929); 6,7,8,9-1H-tetrahydro-1H-imidazo[4,5-c]quinolin-4-amines (e.g., U.S. Pat. No. 5,352,784); 2H-pyrazolo[3,4-c]quinolone-4-amines (e.g., U.S. Pat. No. 7,544,697); and N-1 and 2-substituted 1H-imidazo[4,5-c]quinolin-4-amines (e.g., U.S. Pat. Nos. 6,331,539, 6,451,810, 6,664,264, 8,691,837, 8,088,790, 8,673,932, 8,697,873, 7,915,281).

SUMMARY

New compounds that can be useful in inducing cytokine biosynthesis in animals are disclosed. Such compounds are of the following Formulas I, II, and XXI:

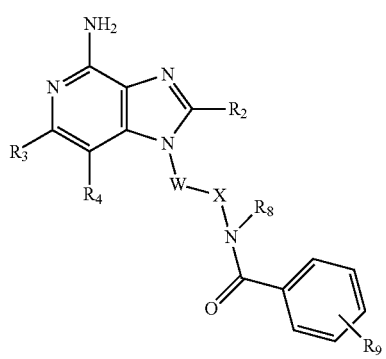

Formula I

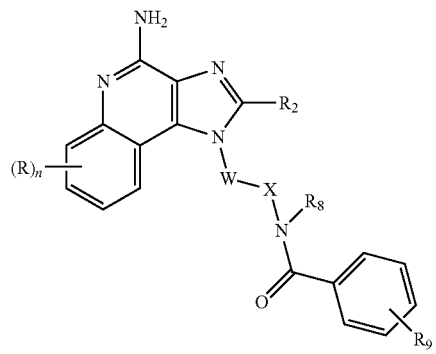

Formula II

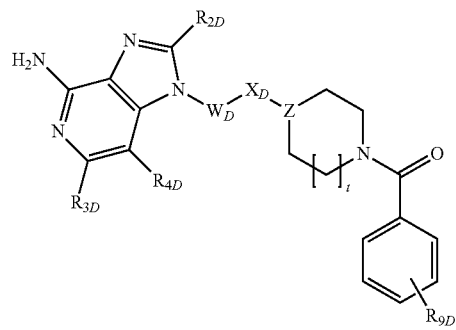

Formula XXI wherein R, $R_2$, $R_{2D}$, $R_3$, $R_{3D}$, $R_4$, $R_{4D}$, $R_8$, $R_9$, $R_{9D}$, W, $W_D$, X, $X_D$, Z, n, and t are as defined below. A common structural feature of the compounds of Formulas I, II, and XXI is the inclusion of a guanidino substituted benzamide group. The guanidino substituent ($R_9$, $R_{9D}$) can be directly attached to either the ortho, meta, or para position of the benzamide ring. Alternatively, the guanidino substituent can be attached to either the ortho, meta, or para position of the benzamide ring via a linker group, such as for example an alkylene linker.

In addition, more specific examples of such compounds include the compounds of Formulas III-XXIV which are defined below, as well as salts, particularly pharmaceutically acceptable salts, thereof.

The compounds and salts, such as pharmaceutically acceptable salts, of Formulas I-XXIV can be useful as immune response modifiers due to their ability to induce cytokine biosynthesis (e.g., induce the synthesis of at least one cytokine) and otherwise modulate the immune response when administered to animals. The compounds can therefore be useful in the treatment of a variety of conditions such as viral diseases and tumors that are responsive to such changes in the immune response.

Pharmaceutical compositions containing an effective amount of one or more compounds of Formulas I-XXIV and salts, particularly pharmaceutically acceptable salts, thereof are disclosed. Also disclosed are methods of inducing cytokine biosynthesis in an animal, treating a viral disease in an animal, and treating a neoplastic disease in an animal by administering to the animal one or more compounds from Formulas I-XXIV and/or pharmaceutically acceptable salts thereof.

Methods for synthesizing compounds of Formulas I-XXIV are provided.

The above summary of the present invention is not intended to describe each disclosed embodiment or every implementation of the present invention. The description that follows more particularly exemplifies illustrative embodiments. In several places throughout the description, guidance is provided through lists of examples, which can be used in various combinations. In each instance, the recited list serves only as a representative group and should not be interpreted as an exhaustive list.

DETAILED DESCRIPTION

As used herein, "a", "an", "the", "at least one", and "one or more" are used interchangeably and are intended to include both the singular and the plural except in cases where the singular alone is specifically called for or clearly required by the context.

As used herein, "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Ph" is used as an abbreviation for a phenyl group.

As used herein, "pharmaceutically acceptable carriers" include those carriers that can deliver therapeutically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co. and can be readily selected by one of ordinary skill in the art.

"Therapeutically effective amount" and "effective amount" are defined as an amount of compound or salt sufficient to induce a therapeutic or prophylactic effect, such a cytokine induction, immunomodulation, antitumor activity, and/or antiviral activity.

"Independently," when used to describe the identity of one or more variable reference elements (such as when used in the phrase "independently selected" or "independently selected from the group"), means that each occurrence of any of the variable elements may have the same or different identity, within the specified limitations, regardless of the identity of any other occurrence of the reference element(s). Thus, if there are two occurrences of reference element "A," and reference element "A" can be independently selected from identity "B" or identity "C", each of the two occurrences of "A" can be either "B" or "C", in any combination (e.g., "B,B"; "B,C"; "C,B"; or "C,C"). Alternatively, if there are two different reference elements (reference element "D" and reference element "E") that can occur together and reference element "D" and reference element "E" can each be independently selected from identity "F" or identity "G", then each occurrence of "D" can be "F" or "G" and likewise each occurrence of "E" can be "F" or "G", to produce any combination of "D" and "E" (e.g., "D"="F" and "E"="F"; "D"="F" and "E"="G"; "D"="G" and "E"="F"; or "D"="G" and "E"="G".

The terms "alkyl", "alkenyl", "alkynyl" and the prefix "alk-" are inclusive of straight chain groups, branched chain groups, cyclic groups, and combinations thereof, e.g. cycloalkyl and cycloalkenyl. Alkyl groups are saturated aliphatic hydrocarbons. Alkenyl groups are unsaturated aliphatic hydrocarbons having one or more carbon-carbon double bonds. Alkynyl groups are unsaturated aliphatic hydrocarbons having one or more carbon-carbon triple bonds. Unless otherwise specified, these groups contain from 1 to 14 carbon atoms, with alkenyl groups containing from 2 to 14 carbon atoms and alkynyl groups containing from 2-14 atoms. In some embodiments, these groups have a total of up to 14 carbon atoms, up to 12 carbon atoms, up to 10 carbon atoms, up to 8 carbon atoms, up to 6 carbon atoms, up to 5 carbon atoms, up to 4 carbon atoms, up to 3 carbon atoms, or up to 2 carbon atoms. In some embodiments, these groups have at least 1 carbon atom, at least 2 carbon atoms, at least 3 carbon atoms, or at least 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, norbornenyl, and the like The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, pentafluoroethyl and the like.

Unless otherwise specified, "alkylene", "alkenylene", and "alkynylene" are the diradical equivalents of the "alkyl", "alkenyl", and "alkynyl" defined above. The terms, "alkylenyl", "alkenylenyl", and "alkynylenyl" are used when "alkylene", "alkenylene", and "alkynylene" respectively, are substituted. For example, an alkoxyalkylenyl group comprises an alkylene moiety to which an alkoxy group is attached (e.g., —CH$_2$OCH$_3$, —CH$_2$CH$_2$OCH$_3$, —CH$_2$OCH$_2$CH$_3$, etc.). As a further example, a hydroxyalkylenyl group comprises an alkylene moiety to which a hydroxyl group is attached (e.g., —CH$_2$OH, —CH$_2$CH$_2$OH, etc.). As yet another example arylalkylenyl group comprises an alkylene moiety to which an aryl group is attached [e.g., —CH$_2$Ph, —CH$_2$CH$_2$Ph, etc.].

An alkylene group with carbon atoms optionally "interrupted" by one or more —O— groups refers to having carbon atoms on either side of the —O—. Examples include —CH$_2$CH$_2$—O—CH$_2$CH$_2$—, —CH$_2$—CH$_2$—O—CH$_2$—CH$_2$—O—CH$_2$CH$_2$—, —(CH$_2$)$_{2-4}$—(OCH$_2$CH$_2$—)$_{1-5}$, —(CH$_2$)$_{2-6}$—(OCH$_2$C$_2$CH$_2$—)$_{1-4}$, etc.

Some examples of alkylamino groups include —NHCH$_3$, —NHCH$_2$CH$_3$, —NHCH(CH$_3$)$_2$, etc. It is understood that the two alkyl groups of a dialkylamino group can be the same or different alkyl groups. Some examples of dialkylamino groups include —N(CH$_3$)$_2$, —N(CH$_2$CH$_3$)$_2$, —N(CH$_3$)(CH$_2$CH$_3$), —N(CH$_3$)(CH$_2$CH$_2$CH$_3$), etc.

Some examples of alkylaminoalkylenyl groups include —CH$_2$NHCH$_3$, —CH$_2$NHCH$_2$CH$_3$, —CH$_2$CH$_2$NHCH$_3$, etc.

Some examples of benzyloxyalkylenyl groups include —CH$_2$OCH$_2$Ph, —CH$_2$CH$_2$OCH$_2$Ph, —CH$_2$CH$_2$CH$_2$OCH$_2$Ph, etc.

Some examples of —C(O)—O-alkyl include —C(O)—O—CH$_3$, —C(O)—O—CH$_2$CH$_3$, —C(O)—O—CH$_2$CH$_2$CH$_3$, —C(O)—O—C(CH$_3$)$_3$, etc.

The term "aryl" as used herein includes carbocyclic aromatic rings or ring systems. Examples of aryl groups include phenyl (designated by the abbreviation "Ph" herein), naphthyl, and biphenyl.

The term "heteroaryl" includes aromatic rings or ring systems that contain at least one ring heteroatom (e.g. O, S, N). In some embodiments, the term "heteroaryl" includes a ring or ring system that contains 2-12 carbon atoms, 1-3 rings, 1-4 heteroatoms, with O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, quinoxalinyl, benzothiazolyl, napthyridinyl, ixoxazolyl, isothiazolyl, purinyl, quinazolinyl, pyrazinyl, 1-oxidopyridyl, pyridazinyl, triazinyl, tetrazinyl, oxadiazolyl, thiadiazolyl, and the like. Preferred heteroaryl groups include, thienyl, pyridyl, quinolinyl, indolyl and imidazolyl.

The terms "arylene", "-arylene-", "heteroarylene", and "-heteroarylene-" are the diradical equivalents of the "aryl" and "heteroaryl" groups defined above. The terms "arylenyl" and "heteroarylenyl" are used when "arylene" and "heteroarylene" are substituted. For example, an alkylarylenyl group comprises an arylene moiety to which an alkyl group is attached (e.g., -Ph-CH$_3$).

The term "compound" includes not only the specific structural formula as drawn or named, but also its configurational isomers, stereoisomers, such as enantiomers, diastereomers, and meso isomers, as well as combinations of one or more of any of the foregoing, except in cases when a specific isomer, enantiomer, or the like is specifically called out. For those structures that exist as tautomers, the term "compound" is intended to include all tautomers, even when only one is drawn, unless only a single tautomer is explicitly recited.

The "salt" of a compound includes pharmaceutically acceptable salts, such as those described in Berge, Stephen M., "Pharmaceutical Salts", *Journal of Pharmaceutical Sciences*, 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

This disclosure provides compounds of the following Formula I

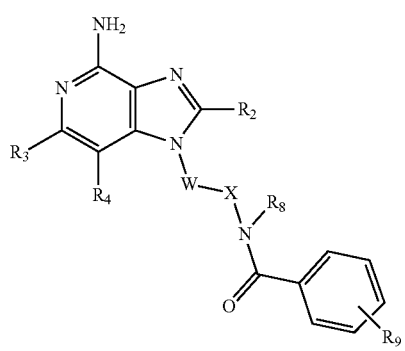

Formula I wherein W, X, $R_2$, $R_3$, $R_4$, $R_8$, and $R_9$ are as defined below; and pharmaceutically acceptable salts thereof.

Examples of compounds of Formula I are more specifically defined by the following Formulas II-V:

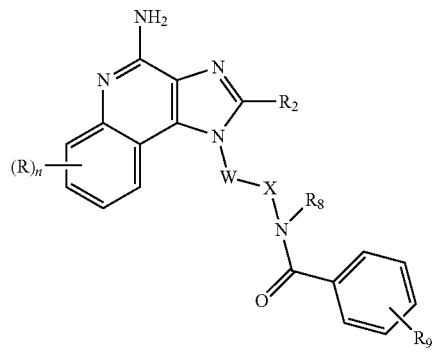

Formula II

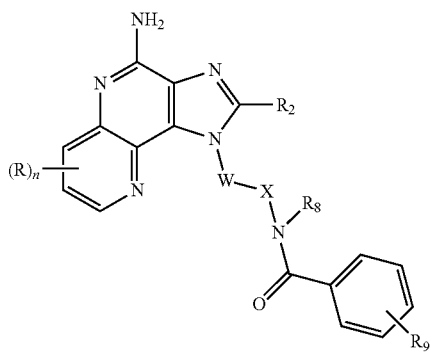

Formula III

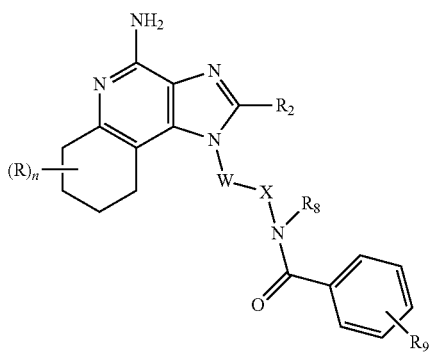

Formula IV

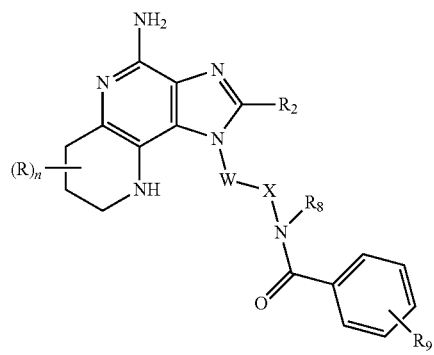

Formula V wherein R, W, X, $R_2$, $R_8$, $R_9$, and n are as defined below as well as salts, particularly pharmaceutically acceptable salts, thereof.

For compounds and salts, such as pharmaceutically acceptable salts, of Formula I, $R_3$ and $R_4$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups.

For compounds and salts, such as pharmaceutically acceptable salts, of Formulas I-V:

R is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

n is an integer from 0 to 2;

W is selected from the group consisting of a covalent bond, —O—, and —NH—;

X is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

R$_9$ is -Q-N(R$_7$)—C(=N—R$_5$)—N(H)R$_6$;

Q is selected from the group consisting of a covalent bond and alkylene;

R$_2$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

R$_7$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

R$_8$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

R$_5$ and R$_6$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula I, R$_3$ and R$_4$ are taken together to form a fused benzene ring, a fused pyridine ring, or a fused cyclohexene ring.

In some embodiments of Formula I, R$_3$ and R$_4$ are taken together to form a fused benzene ring or a fused cyclohexene ring.

In some embodiments of Formula I, R$_3$ and R$_4$ are taken together to form a fused benzene ring or a fused pyridine ring.

In some embodiments of Formula I, R$_3$ and R$_4$ are taken together to form a fused benzene ring.

In some embodiments of Formula I, R$_3$ and R$_4$ are taken together to form a fused benzene ring, a fused pyridine ring, or a fused cyclohexene ring; wherein the fused benzene ring, fused pyridine ring, or fused cyclohexene ring is either unsubstituted or substituted by one and only one R group.

In some embodiments of Formula I, R$_3$ and R$_4$ are taken together to form a fused benzene ring or a fused pyridine ring; wherein the fused benzene ring or fused pyridine ring is either unsubstituted or substituted by one and only one R group.

In some embodiments of Formulas II-V, n is 0 or 1.

In some embodiments of Formulas II-V, n is 0.

In some embodiments of Formulas I-V, R is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.

In some embodiments of Formulas I-V, R is selected from the group consisting of hydroxyl, F, Cl, —CF$_3$, —O—C$_{1-6}$ alkyl, and —C$_{1-6}$ alkyl.

In some embodiments of Formulas I-V, R is selected from the group consisting of hydroxyl, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

In some embodiments of Formulas I-V, R is —C(O)OC$_{1-4}$alkyl.

In some embodiments of Formulas I-V, R is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

In some embodiments of Formulas I-V, R$_2$ is selected from the group consisting hydrogen, alkyl, alkoxyalkylenyl, alkylaminoalkylenyl, and hydroxyalkylenyl.

In some embodiments of Formulas I-V, R$_2$ is selected from the group consisting hydrogen, alkyl, and alkoxyalkylenyl.

In some embodiments of Formulas I-V, R$_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formulas I-V, R$_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formulas I-V, R$_2$ is —CH$_2$NHC(O)CH$_3$ or —CH$_2$NHC(O)cyclopropyl.

In some embodiments of Formulas I-V, R$_2$ is —CH$_2$NHC(O)C$_{1-3}$alkyl.

In some embodiments of Formulas I-V, R$_8$ is selected from the group consisting of hydrogen, alkyl, and arylalkylenyl.

In some embodiments of Formulas I-V, R$_8$ is selected from the group consisting of hydrogen and alkyl.

In some embodiments of Formulas I-V, $R_8$ is selected from the group consisting of hydrogen and $C_{1-4}$alkyl.

In some embodiments of Formulas I-V, $R_8$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, -cyclopentyl, -cyclohexyl, —$CH_2$(cyclopentyl), —$CH_2$(cyclohexyl), and —$CH_2CH_2$—O—$CH_3$.

In some embodiments of Formulas I-V, $R_8$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}Ph$, wherein Ph can be either unsubstituted or substituted with one or more substituents selected from the group consisting of halogen, hydroxyl, alkyl, alkoxy, haloalkyl, and nitrile.

In some embodiments of Formulas I-V, $R_8$ is hydrogen.

In some embodiments of Formulas I-V, $R_7$ is hydrogen, $C_{1-8}$alkyl, or —$CH_2Ph$.

In some embodiments of Formulas I-V, $R_7$ is hydrogen or $C_{1-4}$alkyl.

In some embodiments of Formulas I-V, $R_7$ is hydrogen or $C_{1-2}$alkyl.

In some embodiments of Formulas I-V, $R_7$ is hydrogen.

In some embodiments of Formulas I-V, $R_7$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, -cyclopentyl, -cyclohexyl, —$CH_2$(cyclopentyl), —$CH_2$(cyclohexyl), and —$CH_2CH_2$—O—$CH_3$.

In some embodiments of Formulas I-V, $R_7$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}$ Ph, wherein Ph can be either unsubstituted or substituted with one or more substituents selected from the group consisting of halogen, hydroxyl, alkyl, alkoxy, haloalkyl, and nitrile.

In some embodiments of Formulas I-V, W is a covalent bond or —O—.

In some embodiments of FIGURES I-V, W is a covalent bond.

In some embodiments of Formulas I-V, X is alkylene optionally interrupted by one or more —O— groups.

In some embodiments of Formulas I-V, X is alkylene optionally interrupted or terminated by arylene.

In some embodiments of Formulas I-V, X is a $C_{2-12}$alkylene optionally interrupted by one or more —O— groups.

In some embodiments of Formulas I-V, X is $C_{2-8}$alkylene.
In some embodiments of Formulas I-V, X is $C_{2-6}$alkylene.
In some embodiments of Formulas I-V, X is $C_{2-5}$alkylene.
In some embodiments of Formulas I-V, X is a $C_{2-8}$alkylene optionally interrupted by one or more —O— groups.

In some embodiments of Formulas I-V, X is selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2CH_2$—, —$CH_2CH_2$—O—$CH_2CH_2$—O—$CH_2CH_2$—, —$(CH_2)_{2-4}$—O—$(CH_2)_{2-4}$—, —$(CH_2)_{2-4}$—$(OCH_2CH_2$—$)_{1-5}$, and —$(CH_2)_{2-6}$—$(OCH_2C_2CH_2$—$)_{1-4}$.

In some embodiments of Formulas I-V, X is —$C_{1-5}$-alkylene-arylene-$C_{1-5}$alkylene- or —$C_{1-5}$alkylene-heteroarylene-$C_{1-5}$alkylene-.

In some embodiments of Formulas I-V, X is —$CH_2$-phenylene-$CH_2$—.

In some embodiments of Formulas I-V, W is a bond and X is alkylene optionally interrupted by one or more —O— groups.

In some embodiments of Formulas I-V, W is a bond and X is alkylene.

In some embodiments of Formulas I-V, W is —O— and X is alkylene.

In some embodiments of Formulas I-V, Q is selected from the group consisting of a covalent bond and $C_{1-4}$alkylene.

In some embodiments of Formulas I-V, Q is selected from the group consisting of a covalent bond and $C_{1-2}$alkylene.

In some embodiments of Formulas I-V, Q is selected from the group consisting of a covalent bond and —$CH_2$—.

In some embodiments of Formulas I-V, Q is a covalent bond.

In some embodiments of Formulas I-V, $R_5$ and $R_6$ are independently selected from the group consisting of hydrogen, alkyl, phenyl, and phenylalkylenyl.

In some embodiments of Formulas I-V, $R_5$ and $R_6$ are independently selected from the group consisting of hydrogen, alkyl, cycloalkyl, cycloalkylalkylenyl, aryl, and arylalkylenyl.

In some embodiments of Formulas I-V, $R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas I-V, $R_5$ and $R_6$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}$ $CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$.

In some embodiments of Formulas I-V, $R_5$ and $R_6$ are independently selected from the group consisting of hydrogen, alkyl, -Ph, —$CH_2Ph$, —$CH_2CH_2Ph$, —$(CH_2)_{3-8}Ph$, —$CH_2CH_2$—O-Ph, —$(CH_2)_{3-8}OPh$, —$CH_2CH_2$—O—$CH_2Ph$, —$(CH_2)_{3-8}$ $OCH_2Ph$, and —$(CH_2)_{2-8}$—O—$(CH_2)_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

In some embodiments of Formulas I-V, $R_5$ and $R_6$ are independently selected from the group consisting of hydrogen, —$C(O)OC(CH_3)_3$, and —$C(O)OCH_2Ph$.

In some embodiments of Formulas I-V, $R_5$ is hydrogen and $R_6$ is hydrogen.

In some embodiments of Formulas I-V, $R_5$ is hydrogen, $R_6$ is hydrogen and $R_7$ is hydrogen.

In some embodiments of Formulas I-V, $R_5$ is hydrogen, $R_6$ is hydrogen, $R_7$ is hydrogen and $R_8$ is hydrogen.

In some embodiments of Formulas I-V, $R_5$ is alkyl and $R_6$ is alkyl.

In some embodiments of Formulas I-V, $R_5$ is $C_{1-8}$alkyl and $R_6$ is $C_{1-8}$alkyl.

In some embodiments of Formulas I-V, $R_5$ is $C_{1-4}$alkyl and $R_6$ is $C_{1-4}$alkyl.

In some embodiments of Formulas I-V, X is alkylene optionally interrupted by one or more —O— groups; and $R_2$ is selected from the group consisting of hydrogen, alkyl, and alkoxyalkylenyl.

In some embodiments of Formulas II-V, W is a covalent bond; X is alkylene optionally interrupted by one or more —O— groups; $R_2$ is selected from the group consisting of hydrogen, alkyl, and alkoxyalkylenyl; n is 0 or 1; R is selected from the group consisting of halogen, hydroxyl, alkyl, alkoxy, and haloalkyl; and $R_8$ is selected from the group consisting of hydrogen, alkyl, and arylalkylenyl.

In some embodiments of Formulas I-V, W is a covalent bond; X is alkylene; $R_2$ is selected from the group consisting of hydrogen, alkyl, and alkoxyalkylenyl.

In some embodiments of Formulas I-V, W is a covalent bond; X is alkylene optionally interrupted by one or more —O— groups; $R_2$ is selected from the group consisting of hydrogen, alkyl, and alkoxyalkylenyl; $R_5$ and $R_6$ are independently selected from the group consisting of hydrogen and alkyl; $R_8$ is selected from the group consisting of hydrogen, alkyl, and arylalkylenyl; Q is selected form the group consisting of a covalent bond and —CH$_2$—; $R_7$ is selected from the group consisting of hydrogen and alkyl.

In some embodiments of Formulas I-V, W is a covalent bond; X is alkylene; $R_5$ is alkyl; $R_6$ is alkyl; $R_2$ is selected from the group consisting of hydrogen, alkyl, and alkoxyalkylenyl.

In some embodiments of Formulas I-V, the compound is present in the form of a salt.

The salt is typically a pharmaceutically acceptable salt. Most commonly the salt is a hydrochloride or dihydrochloride salt.

The disclosure also provides compounds of the following Formulas VI-XIII:

Formula VI

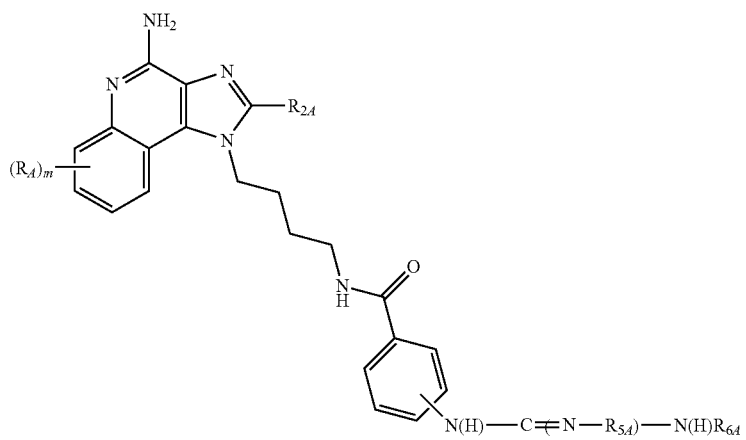

Formula VII

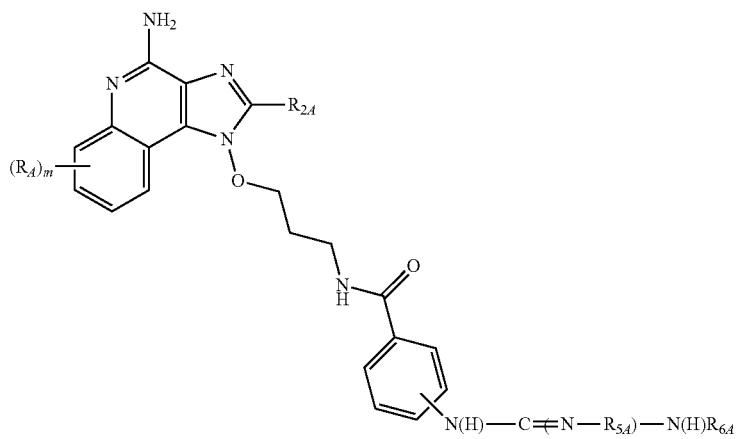

Formula VIII
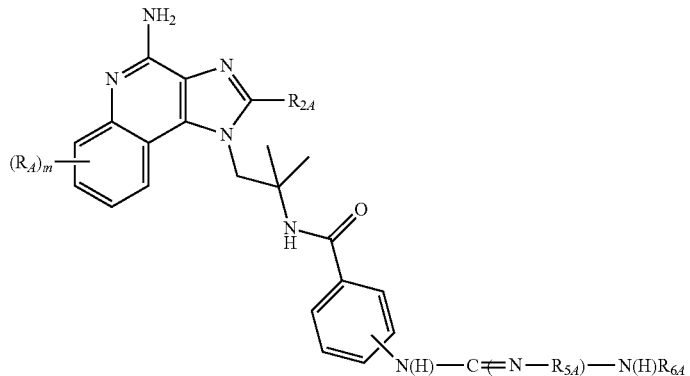
Formula IX
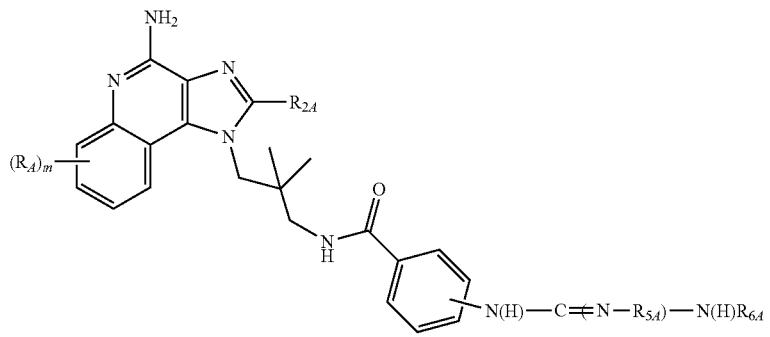
Formula X
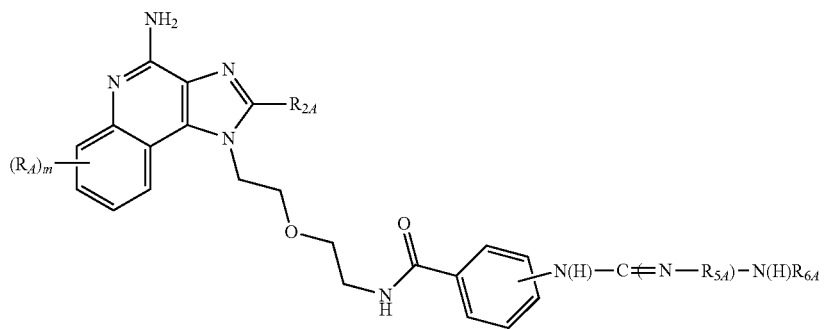
Formula XI
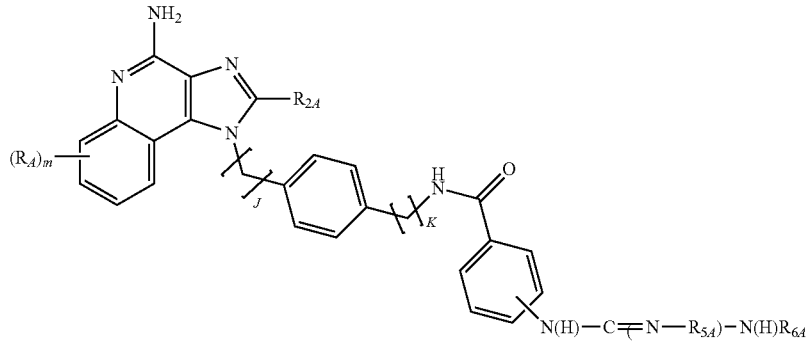

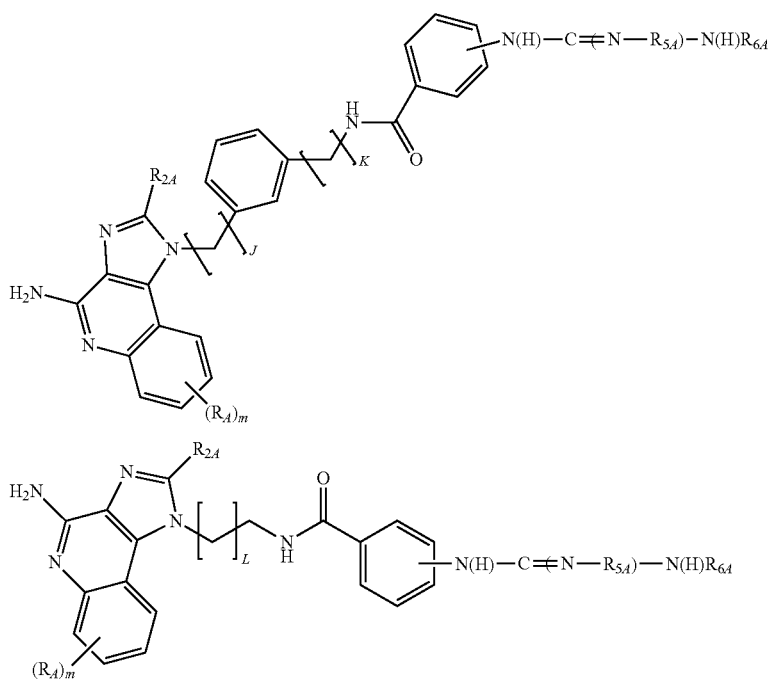

Formula XII

Formula XIII wherein $R_A$, $R_{2A}$, $R_{5A}$, $R_{6A}$, m, J, K, and L are defined for Formulas VI-XIII below; and pharmaceutically acceptable salts thereof.

For the compounds of Formulas VI-XIII:
m is an integer from 0 to 2;
J is an integer from 1 to 5;
K is an integer from 0 to 7;
L is an integer from 1 to 9;
$R_A$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;
$R_{2A}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;
$R_{5A}$ and $R_{6A}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas VI-XIII, m is 0 or 1.
In some embodiments of Formulas VI-XIII, m is 0.
In some embodiments of Formulas XI-XII, J is 1 and K is an integer from 0 to 4.
In some embodiments of Formulas XI-XII, K is 1 and J is an integer from 1 to 4.
In some embodiments of Formulas XI-XII, K is 1 and J is 1.
In some embodiments of Formula XIII, L is an integer from 1 to 10.
In some embodiments of Formula XIII, L is an integer from 1 to 6.
In some embodiments of Formula XIII, L is an integer from 1 to 4.
In some embodiments of Formula XIII, L is an integer from 1 to 2.
In some embodiments of Formulas VI-XIII, $R_A$ is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.
In some embodiments of Formulas VI-XIII, $R_A$ is selected from the group consisting of halogen, hydroxyl, alkyl, alkoxy, and haloalkyl.
In some embodiments of Formulas VI-XIII, $R_{2A}$ is selected from the group consisting hydrogen, alkyl, alkoxyalkylenyl, alkylaminoalkylenyl, and hydroxyalkylenyl.
In some embodiments of Formulas VI-XIII, $R_{2A}$ is selected from the group consisting hydrogen, alkyl, and alkoxyalkylenyl.
In some embodiments of Formulas VI-XIII, $R_{2A}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formulas VI-XIII, $R_{2A}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

In some embodiments of Formulas VI-XIII, $R_{2A}$ is —$CH_2NHC(O)CH_3$ or —$CH_2NHC(O)$cyclopropyl.

In some embodiments of Formulas VI-XIII, $R_{2A}$ is —$CH_2NHC(O)C_{1-3}$alkyl.

In some embodiments of Formulas VI-XIII, $R_{5A}$ and $R_{6A}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas VI-XIII, $R_{5A}$ and $R_{6A}$ are independently selected from the group consisting of hydrogen, alkyl, phenyl, and phenylalkylenyl.

In some embodiments of Formulas VI-XIII, $R_{5A}$ and $R_{6A}$ are independently selected from the group consisting of hydrogen, alkyl, cycloalkyl, cycloalkylalkylenyl, aryl, and arylalkylenyl.

In some embodiments of Formulas VI-XIII, $R_{5A}$ and $R_{6A}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2OCH_3$, —$(CH_2)_{3-8}$—O—$CH_3$, and —$CH_2CH_2CH_2N(CH_3)_2$.

In some embodiments of Formulas VI-XIII, $R_{5A}$ and $R_{6A}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

In some embodiments of Formulas VI-XIII, $R_{5A}$ and $R_{6A}$ are independently selected from the group consisting of hydrogen, —$C(O)OC(CH_3)_3$, and —$C(O)OCH_2Ph$.

In some embodiments of Formulas VI-XIII, $R_{5A}$ hydrogen and $R_{6A}$ is hydrogen.

In some embodiments of Formulas VI-XIII, $R_{5A}$ is alkyl and $R_{6A}$ is alkyl.

In some embodiments of Formulas VI-XIII, $R_{5A}$ is $C_{1-8}$alkyl and $R_{6A}$ is $C_{1-8}$alkyl.

In some embodiments of Formulas VI-XIII, $R_{5A}$ is $C_{1-4}$alkyl and $R_{6A}$ is $C_{1-4}$ alkyl.

In some embodiments of Formulas VI-XIII, the compound is present in the form of a salt. The salt is typically a pharmaceutically acceptable salt. Most commonly the salt is a hydrochloride or dihydrochloride salt.

This disclosure also provides compounds of the following Formula XIV:

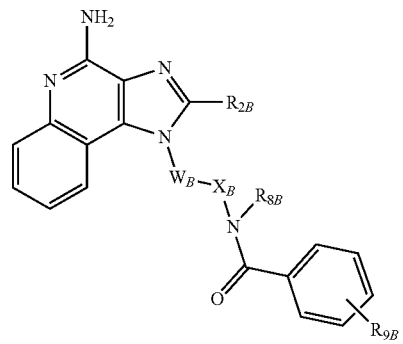

Formula XIV wherein $W_B$, $X_B$, $R_{2B}$, $R_{8B}$ and $R_{9B}$ are as defined below; as well as salts thereof, which are typically pharmaceutically acceptable salts.

For compounds and salts, such as pharmaceutically acceptable salts, of Formula XIV:

$W_B$ is selected from the group consisting of a covalent bond, —O—, and —NH—;

$X_B$ is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

$R_{9B}$ is -$Q_B$-N($R_{7B}$)—C(=N—$R_{5B}$)—N(H)$R_{6B}$;

$Q_B$ is selected from the group consisting of a covalent bond and alkylene;

$R_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2NHC(O)$-alkyl; $R_{8B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{7B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{5B}$ and $R_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XIV, $R_{2B}$ is selected from the group consisting hydrogen, alkyl, alkoxyalkylenyl, alkylaminoalkylenyl, and hydroxyalkylenyl.

In some embodiments of Formula XIV, $R_{2B}$ is selected from the group consisting hydrogen, alkyl, and alkoxyalkylenyl.

In some embodiments of Formula XIV, $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, —$CH_2CH_2OH$, and —$CH_2NHOCH_3$.

In some embodiments of Formula XIV, $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

In some embodiments of Formula XIV, $R_{2B}$ is —$CH_2NHC(O)CH_3$ or —$CH_2NHC(O)$cyclopropyl.

In some embodiments of Formula XIV, $R_{2B}$ is —$CH_2NHC(O)C_{1-3}$alkyl.

In some embodiments of Formula XIV, $R_{8B}$ is selected from the group consisting of hydrogen, alkyl, and arylalkylenyl.

In some embodiments of Formula XIV, $R_{8B}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_3$, —$CH_2CH_2CH(CH_3)_2$, -cyclopentyl, -cyclohexyl, —$CH_2$(cyclopentyl), —$CH_2$(cyclohexyl), and —$CH_2CH_2$—O—$CH_3$.

In some embodiments of Formula XIV, $R_{8B}$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}$ Ph, wherein Ph can be either unsubstituted or substituted with one or more substituents selected from the group consisting of halogen, hydroxyl, alkyl, alkoxy, haloalkyl, and nitrile.

In some embodiments of Formula XIV, $R_{8B}$ is selected from the group consisting of hydrogen and alkyl.

In some embodiments of Formula XIV, $R_{8B}$ is selected from the group consisting of hydrogen and $C_{1-4}$alkyl.

In some embodiments of Formula XIV, $R_{8B}$ is hydrogen.

In some embodiments of Formula XIV, $R_{7B}$ is hydrogen, $C_{1-8}$alkyl, or —$CH_2Ph$.

In some embodiments of Formula XIV, $R_{7B}$ is hydrogen or $C_{1-4}$alkyl.

In some embodiments of Formula XIV, $R_{7B}$ is hydrogen.

In some embodiments of Formula XIV, $R_{7B}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_3$, —$CH_2CH_2CH(CH_3)_2$, cyclopentyl, -cyclohexyl, —$CH_2$(cyclopentyl), —$CH_2$(cyclohexyl), and —$CH_2CH_2$—O—$CH_3$.

In some embodiments of Formula XIV, $R_{7B}$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}$ Ph, wherein Ph can be either unsubstituted or substituted with one or more substituents selected from the group consisting of halogen, hydroxyl, alkyl, alkoxy, haloalkyl, and nitrile.

In some embodiments of Formula XIV, $R_{5B}$ and $R_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XIV, $R_{5B}$ and $R_{6B}$ are independently selected from the group consisting of hydrogen, alkyl, phenyl, and phenylalkylenyl.

In some embodiments of Formula XIV, $R_{5B}$ and $R_{6B}$ are independently selected from the group consisting of hydrogen, alkyl, cycloalkyl, cycloalkylalkylenyl, aryl, and arylalkylenyl.

In some embodiments of Formula XIV, $R_{5B}$ and $R_{6B}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$(CH_2)_{3-8}$—O—$CH_3$, —$CH_2CH_2OCH_3$, and —$CH_2CH_2CH_2N(CH_3)_2$.

In some embodiments of Formula XIV, $R_{5B}$ and $R_{6B}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

In some embodiments of Formula XIV, $R_{5A}$ and $R_{6A}$ are independently selected from the group consisting of hydrogen, —$C(O)OC(CH_3)_3$, and —$C(O)OCH_2Ph$.

In some embodiments of Formula XIV, $R_{5B}$ is hydrogen and $R_{6B}$ is hydrogen.

In some embodiments of Formula XIV, $R_{5B}$ is hydrogen, $R_{6B}$ is hydrogen and $R_{7B}$ is hydrogen.

In some embodiments of Formula XIV, $R_{5B}$ is hydrogen, $R_{6B}$ is hydrogen, $R_{7B}$ is hydrogen and $R_{8B}$ is hydrogen.

In some embodiments of Formula XIV, $R_{5B}$ is alkyl and $R_{6B}$ is alkyl.

In some embodiments of Formula XIV, $R_{5B}$ is $C_{1-8}$alkyl and $R_{6B}$ is $C_{1-8}$alkyl.

In some embodiments of Formula XIV, $R_{5B}$ is $C_{1-4}$ alkyl and $R_{6B}$ is $C_{1-4}$ alkyl.

In some embodiments of Formula XIV, $W_B$ is a covalent bond or —O—.

In some embodiments of Formula XIV, $W_B$ is a covalent bond.

In some embodiments of Formula XIV, $X_B$ is alkylene optionally interrupted by one or more —O— groups.

In some embodiments of Formulas XIV, $X_B$ is alkylene optionally interrupted or terminated by arylene.

In some embodiments of Formula XIV, $X_B$ is a $C_{2-12}$alkylene optionally interrupted by one or more —O— groups.

In some embodiments of Formula XIV, $X_B$ is a $C_{2-8}$alkylene optionally interrupted by one or more —O— groups.

In some embodiments of Formula XIV, $X_B$ is $C_{2-8}$alkylene.

In some embodiments of Formula XIV, $X_B$ is $C_{2-6}$alkylene.

In some embodiments of Formula XIV, $X_B$ is $C_{2-8}$alkylene.

In some embodiments of Formula XIV, $X_B$ is selected from the group consisting of —$CH_2CH_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$—O—CH$_2$CH$_2$—, —(CH$_2$)$_{2-4}$—(OCH$_2$CH$_2$—)$_{1-5}$, and, —(CH$_2$)$_{2-6}$—(OCH$_2$C$_2$CH$_2$—)$_{1-4}$.

In some embodiments of Formula XIV, $X_B$ is —C$_{1-5}$alkylene-arylene-C$_{1-5}$alkylene- or —C$_{1-5}$alkylene-heteroarylene-C$_{1-5}$alkylene-.

In some embodiments of Formula XIV, $X_B$ is —CH$_2$-phenylene-CH$_2$—.

In some embodiments of Formula XIV, $W_B$ is a bond and $X_B$ is alkylene optionally interrupted by one or more —O— groups.

In some embodiments of Formula XIV, $W_B$ is a bond and $X_B$ is alkylene.

In some embodiments of Formula XIV, $W_B$ is —O— and $X_B$ is alkylene.

In some embodiments of Formula XIV, $Q_B$ is selected from the group consisting of a covalent bond and C$_{1-4}$alkylene.

In some embodiments of Formula XIV, $Q_B$ is selected from the group consisting of a covalent bond and C$_{1-2}$alkylene.

In some embodiments of Formula XIV, $Q_B$ is selected from the group consisting of a covalent bond and —CH$_2$—.

In some embodiments of Formula XIV, $Q_B$ is a covalent bond.

In some embodiments of Formula XIV, $W_B$ is a bond; $X_B$ is alkylene optionally interrupted by one or more —O— groups; $R_{2B}$ is selected from the group consisting of hydrogen, alkyl, and alkoxyalkylenyl.

In some embodiments of Formula XIV, $W_B$ is a bond; $X_B$ is alkylene; $R_{2B}$ is selected from the group consisting of hydrogen, alkyl, and alkoxyalkylenyl.

In some embodiments of Formula XIV, $W_B$ is a bond; $X_B$ is alkylene optionally interrupted by one or more —O— groups; $R_{5B}$ and $R_{6B}$ are independently selected from the group consisting of hydrogen and alkyl; $R_{2B}$ is selected from the group consisting of hydrogen, alkyl, and alkoxyalkylenyl.

In some embodiments of Formula XIV, $W_B$ is a bond; $X_B$ is alkylene; $R_{5B}$ and $R_{6B}$ are independently selected from the group consisting of hydrogen and alkyl; $R_{2B}$ is selected from the group consisting of hydrogen, alkyl, and alkoxyalkylenyl.

In some embodiments of Formula XIV, $W_B$ is a bond; $X_B$ is alkylene optionally interrupted by one or more —O— groups; $R_{5B}$ is alkyl; $R_{6B}$ is alkyl; $R_{2B}$ is selected from the group consisting of hydrogen, alkyl, and alkoxyalkylenyl.

In some embodiments of Formula XIV, $W_B$ is a bond; $X_B$ is alkylene; $R_{5B}$ is alkyl; $R_{6B}$ is alkyl; $R_{2B}$ is selected from the group consisting of hydrogen, alkyl, and alkoxyalkylenyl.

In some embodiments of Formula XIV, the compound is present in the form of a salt. The salt is typically a pharmaceutically acceptable salt. Most commonly the salt is a hydrochloride or dihydrochloride salt.

The disclosure provides a method of inducing cytokine biosynthesis in an animal comprising administering to the animal an effective amount of a compound or salt selected from the group consisting of any one of the above embodiments of Formulas I-XIV.

The disclosure provides a method of inducing IFN-alpha biosynthesis in an animal by administering to the animal an effective amount of a compound or salt selected from any one of the above embodiments of Formulas I-XIV.

The disclosure provides a method of inducing IFN-gamma biosynthesis in an animal by administering to the animal an effective amount of a compound or salt selected from any one of the above embodiments of Formulas IXIV.

The disclosure provides a method of inducing TNF-alpha biosynthesis in an animal by administering to the animal an effective amount of a compound or salt selected from any one of the above embodiments of Formulas I-XIV.

The disclosure provides a method of inducing IP-10 biosynthesis in an animal by administering to the animal an effective amount of a compound or salt selected from any one of the above embodiments of Formulas I-XIV.

The disclosure also provides a method of treating a viral disease in an animal by administering to the animal an effective amount of a compound or salt selected from any one of the above embodiments of Formulas I-XIV.

The disclosure also provides a method of treating a neoplastic disease in an animal by administering to the animal an effective amount of a compound or salt selected from any one of the above embodiments of Formulas I-XIV.

This disclosure also provides compounds of the following Formulas XV-XX:

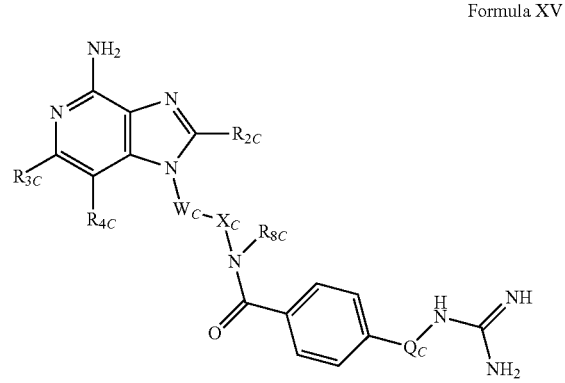

Formula XV

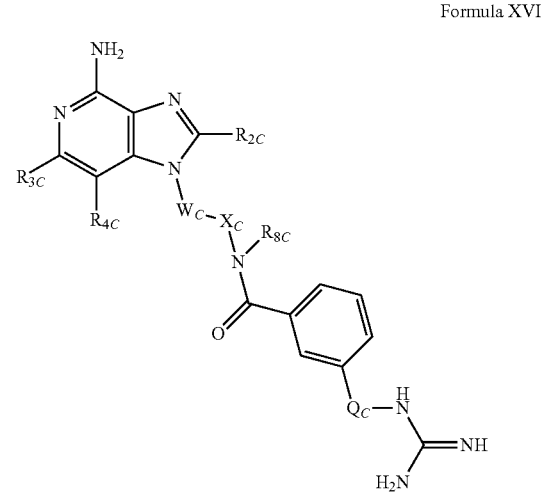

Formula XVI

Formula XVII

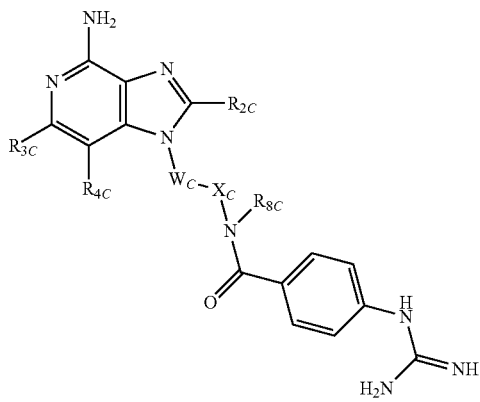

Formula XVIII

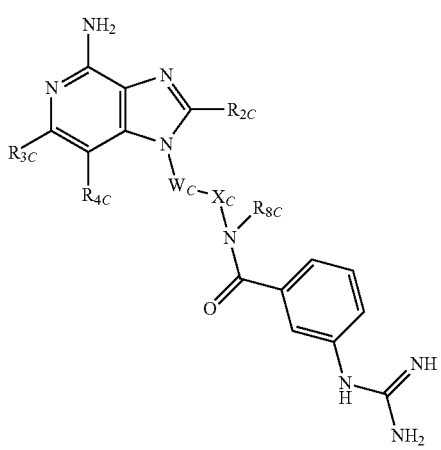

Formula XIX

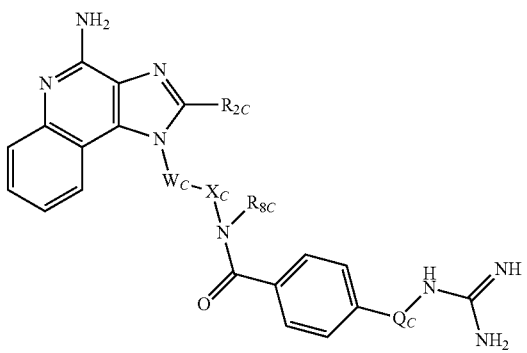

Formula XX

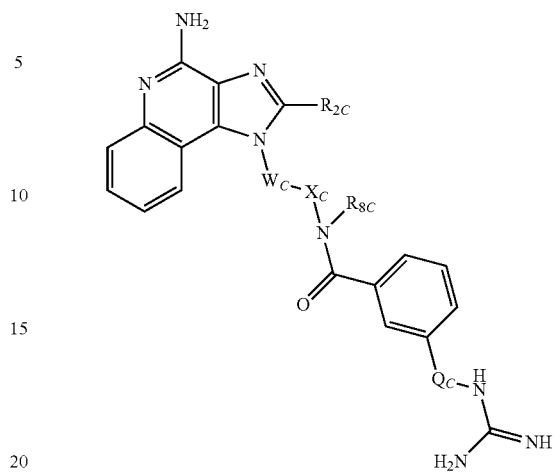

wherein $W_C$, $X_C$, $R_{2C}$, $R_{3C}$, $R_{4C}$, $R_{8C}$, and $Q_C$ are as defined below; and pharmaceutically acceptable salts thereof.

For compounds and salts, such as pharmaceutically acceptable salts, of Formulas XV-XVIII, $R_{3C}$ and $R_{4C}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more $R_C$ groups.

For compounds and salts, such as pharmaceutically acceptable salts, of Formulas XV-XVIII, $R_C$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile.

For compounds and salts, such as pharmaceutically acceptable salts, of Formulas XV-XX:

$W_C$ is selected from the group consisting of a covalent bond, —O—, and —NH—;

$X_C$ is selected from the group consisting of alkylene, alkenylene, and alkynylene, wherein any of the alkylene, alkenylene, and alkynylene groups can be optionally interrupted by one or more —O— groups;

$Q_C$ is selected from the group consisting of a covalent bond and alkylene;

$R_{2C}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{8C}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

In some embodiments of Formulas XV-XVIII, $R_{3C}$ and $R_{4C}$ are taken together to form a fused benzene ring, a fused pyridine ring, or a fused cyclohexene ring.

In some embodiments of Formulas XV-XVIII, $R_{3C}$ and $R_{4C}$ are taken together to form a fused benzene ring or a fused cyclohexene ring.

In some embodiments of Formulas XV-XVIII, $R_{3C}$ and $R_{4C}$ are taken together to form a fused benzene ring or a fused pyridine ring.

In some embodiments of Formulas XV-XVIII, $R_{3C}$ and $R_{4C}$ are taken together to form a fused benzene ring.

In some embodiments of Formulas XV-XVIII, $R_{3C}$ and $R_{4C}$ are taken together to form a fused benzene ring, a fused pyridine ring, or a fused cyclohexene ring; wherein the fused benzene ring, fused pyridine ring, or fused cyclohexene ring is either unsubstituted or substituted by one and only one $R_C$ group.

In some embodiments of Formulas XV-XVIII, $R_{3C}$ and $R_{4C}$ are taken together to form a fused benzene ring or a fused pyridine ring; wherein the fused benzene ring or fused pyridine ring is either unsubstituted or substituted by one and only one $R_C$ group.

In some embodiments of Formulas XV-XX, $W_C$ is a covalent bond and $X_C$ is alkylene optionally interrupted by one or more —O— groups.

In some embodiments of Formulas XV-XX, —$W_C$—$X_C$— is —O—$C_{2-7}$alkylene- or —$C_{2-8}$alkylene-.

In some embodiments of Formulas XV-XX, —$W_C$—$X_C$— is —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, or —$CH_2CH_2$—O—$CH_2CH_2$—.

In some embodiments of Formulas XV-XX, $R_{2C}$ is selected from the group consisting hydrogen, alkyl, alkoxyalkylenyl, alkylaminoalkylenyl, and hydroxyalkylenyl.

In some embodiments of Formulas XV-XX, $R_{2C}$ is selected from the group consisting hydrogen, alkyl, and alkoxyalkylenyl.

In some embodiments of Formulas XV-XX, $R_{2C}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, —$CH_2CH_2OH$, and —$CH_2NHOCH_3$.

In some embodiments of Formulas XV-XX, $R_{2C}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

In some embodiments of Formulas XV-XX, $Q_C$ is selected from the group consisting of a covalent bond and $C_{1-4}$alkylene.

In some embodiments of Formulas XV-XX, $Q_C$ is selected from the group consisting of a covalent bond and $C_{1-2}$alkylene.

In some embodiments of Formulas XV-XX, $Q_C$ is selected from the group consisting of a covalent bond and —$CH_2$—.

In some embodiments of Formulas XV-XX, $Q_C$ is a covalent bond.

In some embodiments of Formulas XV-XX, $R_{8C}$ is selected from the group consisting of hydrogen, alkyl, and arylalkylenyl.

In some embodiments of Formulas XV-XX, $R_{8C}$ is selected from the group consisting of hydrogen and alkyl.

In some embodiments of Formulas XV-XX, $R_{8C}$ is selected from the group consisting of hydrogen and $C_{1-4}$alkyl.

In some embodiments of Formulas XV-XX, $R_{8C}$ is hydrogen.

In some embodiments of Formulas XV-XX, $W_C$ is selected from the group consisting of a covalent bond and —O—; $X_C$ is alkylene optionally interrupted by one or more —O— groups; $R_{2C}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

Exemplary compounds of Formulas XIX and XX are presented in Tables 1-12. In the Tables 1-12, each row represents a specific compound with $W_C$, $X_C$, $R_{2C}$, $R_{8C}$, and $Q_C$ defined.

TABLE 1

| $W_C$ | $X_C$ | $R_{2C}$ | $R_{8C}$ | $Q_C$ |
|---|---|---|---|---|
| covalent bond | —$(CH_2)_2$— | H | H | covalent bond |
| covalent bond | —$(CH_2)_3$— | H | H | covalent bond |
| covalent bond | —$(CH_2)_4$— | H | H | covalent bond |
| covalent bond | —$(CH_2)_5$— | H | H | covalent bond |
| covalent bond | —$CH_2C(CH_3)_2$— | H | H | covalent bond |
| covalent bond | —$CH_2C(CH_3)_2CH_2$— | H | H | covalent bond |
| covalent bond | —$CH_2CH_2OCH_2CH_2$— | H | H | covalent bond |
| —O— | —$(CH_2)_3$— | H | H | covalent bond |
| —O— | —$(CH_2)_4$— | H | H | covalent bond |

TABLE 2

| $W_C$ | $X_C$ | $R_{2C}$ | $R_{8C}$ | $Q_C$ |
|---|---|---|---|---|
| covalent bond | —$(CH_2)_2$— | —$CH_3$ | H | covalent bond |
| covalent bond | —$(CH_2)_3$— | —$CH_3$ | H | covalent bond |
| covalent bond | —$(CH_2)_4$— | —$CH_3$ | H | covalent bond |
| covalent bond | —$(CH_2)_5$— | —$CH_3$ | H | covalent bond |
| covalent bond | —$CH_2C(CH_3)_2$— | —$CH_3$ | H | covalent bond |
| covalent bond | —$CH_2C(CH_3)_2CH_2$— | —$CH_3$ | H | covalent bond |
| covalent bond | —$CH_2CH_2OCH_2CH_2$— | —$CH_3$ | H | covalent bond |
| —O— | —$(CH_2)_3$— | —$CH_3$ | H | covalent bond |
| —O— | —$(CH_2)_4$— | —$CH_3$ | H | covalent bond |

TABLE 3

| $W_C$ | $X_C$ | $R_{2C}$ | $R_{8C}$ | $Q_C$ |
|---|---|---|---|---|
| covalent bond | —$(CH_2)_2$— | —$CH_2CH_3$ | H | covalent bond |
| covalent bond | —$(CH_2)_3$— | —$CH_2CH_3$ | H | covalent bond |
| covalent bond | —$(CH_2)_4$— | —$CH_2CH_3$ | H | covalent bond |

TABLE 3-continued

| $W_C$ | $X_C$ | $R_{2C}$ | $R_{8C}$ | $Q_C$ |
|---|---|---|---|---|
| covalent bond | —(CH$_2$)$_5$— | —CH$_2$CH$_3$ | H | covalent bond |
| covalent bond | —CH$_2$C(CH$_3$)$_2$— | —CH$_2$CH$_3$ | H | covalent bond |
| covalent bond | —CH$_2$C(CH$_3$)$_2$CH$_2$— | —CH$_2$CH$_3$ | H | covalent bond |
| covalent bond | —CH$_2$CH$_2$OCH$_2$CH$_2$— | —CH$_2$CH$_3$ | H | covalent bond |
| —O— | —(CH$_2$)$_3$— | —CH$_2$CH$_3$ | H | covalent bond |
| —O— | —(CH$_2$)$_4$— | —CH$_2$CH$_3$ | H | covalent bond |

TABLE 4

| $W_C$ | $X_C$ | $R_{2C}$ | $R_{8C}$ | $Q_C$ |
|---|---|---|---|---|
| covalent bond | —(CH$_2$)$_2$— | —CH$_2$CH$_2$CH$_3$ | H | covalent bond |
| covalent bond | —(CH$_2$)$_3$— | —CH$_2$CH$_2$CH$_3$ | H | covalent bond |
| covalent bond | —(CH$_2$)$_4$— | —CH$_2$CH$_2$CH$_3$ | H | covalent bond |
| covalent bond | —(CH$_2$)$_5$— | —CH$_2$CH$_2$CH$_3$ | H | covalent bond |
| covalent bond | —CH$_2$C(CH$_3$)$_2$— | —CH$_2$CH$_2$CH$_3$ | H | covalent bond |
| covalent bond | —CH$_2$C(CH$_3$)$_2$CH$_2$— | —CH$_2$CH$_2$CH$_3$ | H | covalent bond |
| covalent bond | —CH$_2$CH$_2$OCH$_2$CH$_2$— | —CH$_2$CH$_2$CH$_3$ | H | covalent bond |
| —O— | —(CH$_2$)$_3$— | —CH$_2$CH$_2$CH$_3$ | H | covalent bond |
| —O— | —(CH$_2$)$_4$— | —CH$_2$CH$_2$CH$_3$ | H | covalent bond |

TABLE 5

| $W_C$ | $X_C$ | $R_{2C}$ | $R_{8C}$ | $Q_C$ |
|---|---|---|---|---|
| covalent bond | —(CH$_2$)$_2$— | —CH$_2$CH$_2$CH$_2$CH$_3$ | H | covalent bond |
| covalent bond | —(CH$_2$)$_3$— | —CH$_2$CH$_2$CH$_2$CH$_3$ | H | covalent bond |
| covalent bond | —(CH$_2$)$_4$— | —CH$_2$CH$_2$CH$_2$CH$_3$ | H | covalent bond |
| covalent bond | —(CH$_2$)$_5$— | —CH$_2$CH$_2$CH$_2$CH$_3$ | H | covalent bond |
| covalent bond | —CH$_2$C(CH$_3$)$_2$— | —CH$_2$CH$_2$CH$_2$CH$_3$ | H | covalent bond |
| covalent bond | —CH$_2$C(CH$_3$)$_2$CH$_2$— | —CH$_2$CH$_2$CH$_2$CH$_3$ | H | covalent bond |
| covalent bond | —CH$_2$CH$_2$OCH$_2$CH$_2$— | —CH$_2$CH$_2$CH$_2$CH$_3$ | H | covalent bond |
| —O— | —(CH$_2$)$_3$— | —CH$_2$CH$_2$CH$_2$CH$_3$ | H | covalent bond |
| —O— | —(CH$_2$)$_4$— | —CH$_2$CH$_2$CH$_2$CH$_3$ | H | covalent bond |

TABLE 6

| $W_C$ | $X_C$ | $R_{2C}$ | $R_{8C}$ | $Q_C$ |
|---|---|---|---|---|
| covalent bond | —(CH$_2$)$_2$— | —CH$_2$OCH$_2$CH$_3$ | H | covalent bond |
| covalent bond | —(CH$_2$)$_3$— | —CH$_2$OCH$_2$CH$_3$ | H | covalent bond |
| covalent bond | —(CH$_2$)$_4$— | —CH$_2$OCH$_2$CH$_3$ | H | covalent bond |
| covalent bond | —(CH$_2$)$_5$— | —CH$_2$OCH$_2$CH$_3$ | H | covalent bond |
| covalent bond | —CH$_2$C(CH$_3$)$_2$— | —CH$_2$OCH$_2$CH$_3$ | H | covalent bond |
| covalent bond | —CH$_2$C(CH$_3$)$_2$CH$_2$— | —CH$_2$OCH$_2$CH$_3$ | H | covalent bond |
| covalent bond | —CH$_2$CH$_2$OCH$_2$CH$_2$— | —CH$_2$OCH$_2$CH$_3$ | H | covalent bond |
| —O— | —(CH$_2$)$_3$— | —CH$_2$OCH$_2$CH$_3$ | H | covalent bond |
| —O— | —(CH$_2$)$_4$— | —CH$_2$OCH$_2$CH$_3$ | H | covalent bond |

TABLE 7

| $W_C$ | $X_C$ | $R_{2C}$ | $R_{8C}$ | $Q_C$ |
|---|---|---|---|---|
| covalent bond | —(CH$_2$)$_2$— | H | H | —CH$_2$— |
| covalent bond | —(CH$_2$)$_3$— | H | H | —CH$_2$— |
| covalent bond | —(CH$_2$)$_4$— | H | H | —CH$_2$— |
| covalent bond | —(CH$_2$)$_5$— | H | H | —CH$_2$— |
| covalent bond | —CH$_2$C(CH$_3$)$_2$— | H | H | —CH$_2$— |
| covalent bond | —CH$_2$C(CH$_3$)$_2$CH$_2$— | H | H | —CH$_2$— |
| covalent bond | —CH$_2$CH$_2$OCH$_2$CH$_2$— | H | H | —CH$_2$— |
| —O— | —(CH$_2$)$_3$— | H | H | —CH$_2$— |
| —O— | —(CH$_2$)$_4$— | H | H | —CH$_2$— |

TABLE 8

| $W_C$ | $X_C$ | $R_{2C}$ | $R_{8C}$ | $Q_C$ |
|---|---|---|---|---|
| covalent bond | —(CH$_2$)$_2$— | —CH$_3$ | H | —CH$_2$— |
| covalent bond | —(CH$_2$)$_3$— | —CH$_3$ | H | —CH$_2$— |
| covalent bond | —(CH$_2$)$_4$— | —CH$_3$ | H | —CH$_2$— |
| covalent bond | —(CH$_2$)$_5$— | —CH$_3$ | H | —CH$_2$— |
| covalent bond | —CH$_2$C(CH$_3$)$_2$— | —CH$_3$ | H | —CH$_2$— |
| covalent bond | —CH$_2$C(CH$_3$)$_2$CH$_2$— | —CH$_3$ | H | —CH$_2$— |
| covalent bond | —CH$_2$CH$_2$OCH$_2$CH$_2$— | —CH$_3$ | H | —CH$_2$— |
| —O— | —(CH$_2$)$_3$— | —CH$_3$ | H | —CH$_2$— |
| —O— | —(CH$_2$)$_4$— | —CH$_3$ | H | —CH$_2$— |

TABLE 9

| $W_C$ | $X_C$ | $R_{2C}$ | $R_{8C}$ | $Q_C$ |
|---|---|---|---|---|
| covalent bond | —(CH$_2$)$_2$— | —CH$_2$CH$_3$ | H | —CH$_2$— |
| covalent bond | —(CH$_2$)$_3$— | —CH$_2$CH$_3$ | H | —CH$_2$— |
| covalent bond | —(CH$_2$)$_4$— | —CH$_2$CH$_3$ | H | —CH$_2$— |
| covalent bond | —(CH$_2$)$_5$— | —CH$_2$CH$_3$ | H | —CH$_2$— |
| covalent bond | —CH$_2$C(CH$_3$)$_2$— | —CH$_2$CH$_3$ | H | —CH$_2$— |
| covalent bond | —CH$_2$C(CH$_3$)$_2$CH$_2$— | —CH$_2$CH$_3$ | H | —CH$_2$— |
| covalent bond | —CH$_2$CH$_2$OCH$_2$CH$_2$— | —CH$_2$CH$_3$ | H | —CH$_2$— |
| —O— | —(CH$_2$)$_3$— | —CH$_2$CH$_3$ | H | —CH$_2$— |
| —O— | —(CH$_2$)$_4$— | —CH$_2$CH$_3$ | H | —CH$_2$— |

TABLE 10

| $W_C$ | $X_C$ | $R_{2C}$ | $R_{8C}$ | $Q_C$ |
|---|---|---|---|---|
| covalent bond | —(CH$_2$)$_2$— | —CH$_2$CH$_2$CH$_3$ | H | —CH$_2$— |
| covalent bond | —(CH$_2$)$_3$— | —CH$_2$CH$_2$CH$_3$ | H | —CH$_2$— |
| covalent bond | —(CH$_2$)$_4$— | —CH$_2$CH$_2$CH$_3$ | H | —CH$_2$— |
| covalent bond | —(CH$_2$)$_5$— | —CH$_2$CH$_2$CH$_3$ | H | —CH$_2$— |
| covalent bond | —CH$_2$C(CH$_3$)$_2$— | —CH$_2$CH$_2$CH$_3$ | H | —CH$_2$— |
| covalent bond | —CH$_2$C(CH$_3$)$_2$CH$_2$— | —CH$_2$CH$_2$CH$_3$ | H | —CH$_2$— |
| covalent bond | —CH$_2$CH$_2$OCH$_2$CH$_2$— | —CH$_2$CH$_2$CH$_3$ | H | —CH$_2$— |
| —O— | —(CH$_2$)$_3$— | —CH$_2$CH$_2$CH$_3$ | H | —CH$_2$— |
| —O— | —(CH$_2$)$_4$— | —CH$_2$CH$_2$CH$_3$ | H | —CH$_2$— |

TABLE 11

| $W_C$ | $X_C$ | $R_{2C}$ | $R_{8C}$ | $Q_C$ |
|---|---|---|---|---|
| covalent bond | —(CH$_2$)$_2$— | —CH$_2$CH$_2$CH$_2$CH$_3$ | H | —CH$_2$— |
| covalent bond | —(CH$_2$)$_3$— | —CH$_2$CH$_2$CH$_2$CH$_3$ | H | —CH$_2$— |
| covalent bond | —(CH$_2$)$_4$— | —CH$_2$CH$_2$CH$_2$CH$_3$ | H | —CH$_2$— |
| covalent bond | —(CH$_2$)$_5$— | —CH$_2$CH$_2$CH$_2$CH$_3$ | H | —CH$_2$— |
| covalent bond | —CH$_2$C(CH$_3$)$_2$— | —CH$_2$CH$_2$CH$_2$CH$_3$ | H | —CH$_2$— |
| covalent bond | —CH$_2$C(CH$_3$)$_2$CH$_2$— | —CH$_2$CH$_2$CH$_2$CH$_3$ | H | —CH$_2$— |
| covalent bond | —CH$_2$CH$_2$OCH$_2$CH$_2$— | —CH$_2$CH$_2$CH$_2$CH$_3$ | H | —CH$_2$— |
| —O— | —(CH$_2$)$_3$— | —CH$_2$CH$_2$CH$_2$CH$_3$ | H | —CH$_2$— |
| —O— | —(CH$_2$)$_4$— | —CH$_2$CH$_2$CH$_2$CH$_3$ | H | —CH$_2$— |

TABLE 12

| $W_C$ | $X_C$ | $R_{2C}$ | $R_{8C}$ | $Q_C$ |
|---|---|---|---|---|
| covalent bond | —(CH$_2$)$_2$— | —CH$_2$OCH$_2$CH$_3$ | H | —CH$_2$— |
| covalent bond | —(CH$_2$)$_3$— | —CH$_2$OCH$_2$CH$_3$ | H | —CH$_2$— |
| covalent bond | —(CH$_2$)$_4$— | —CH$_2$OCH$_2$CH$_3$ | H | —CH$_2$— |
| covalent bond | —(CH$_2$)$_5$— | —CH$_2$OCH$_2$CH$_3$ | H | —CH$_2$— |
| covalent bond | —CH$_2$C(CH$_3$)$_2$— | —CH$_2$OCH$_2$CH$_3$ | H | —CH$_2$— |
| covalent bond | —CH$_2$C(CH$_3$)$_2$CH$_2$— | —CH$_2$OCH$_2$CH$_3$ | H | —CH$_2$— |
| covalent bond | —CH$_2$CH$_2$OCH$_2$CH$_2$— | —CH$_2$OCH$_2$CH$_3$ | H | —CH$_2$— |
| —O— | —(CH$_2$)$_3$— | —CH$_2$OCH$_2$CH$_3$ | H | —CH$_2$— |
| —O— | —(CH$_2$)$_4$— | —CH$_2$OCH$_2$CH$_3$ | H | —CH$_2$— |

The disclosure provides a method of inducing cytokine biosynthesis in an animal by administering to the animal an effective amount of a compound or salt selected from the group consisting of any one of the above embodiments of Formula XV, Formula XVI, Formula XVII, Formula XVIII, Formula XIX, and Formula XX.

The disclosure also provides a method of inducing cytokine biosynthesis in an animal by administering to the animal an effective amount of a compound or salt selected from the group consisting of any one of the above embodiments of Formula XV, Formula XVI, Formula XVII, Formula XVIII, Formula XIX, and Formula XX; wherein $W_C$ is a covalent bond, $X_C$ is alkylene optionally interrupted by one or more —O— groups, and $R_{2C}$ is selected from the group consisting of hydrogen, alkyl and alkoxyalkylenyl.

The disclosure also provides a method of inducing IFN-alpha biosynthesis in an animal by administering to the animal an effective amount of a compound or salt selected from any one of the above embodiments of Formula XV, Formula XVI, Formula XVII, Formula XVIII, Formula XIX, and Formula XX.

The disclosure also provides a method of inducing IFN-gamma biosynthesis in an animal by administering to the animal an effective amount of a compound or salt selected from any one of the above embodiments of Formula XV, Formula XVI, Formula XVII, Formula XVIII, Formula XIX, and Formula XX.

The disclosure also provides a method of inducing TNF-alpha biosynthesis in an animal by administering to the animal an effective amount of a compound or salt selected from any one of the above embodiments of Formula XV, Formula XVI, Formula XVII, Formula XVIII, Formula XIX, and Formula XX.

The disclosure also provides a method of inducing IP-10 biosynthesis in an animal by administering to the animal an effective amount of a compound or salt selected from any one of the above embodiments of Formula XV, Formula XVI, Formula XVII, Formula XVIII, Formula XIX, and Formula XX.

The disclosure also provides a method for treating a viral disease in an animal by administering to the animal an effective amount of a compound or salt selected from the group consisting of any one of the above embodiments of Formula XV, Formula XVI, Formula XVII, Formula XVIII, Formula XIX, and Formula XX.

The disclosure also provides a method for treating a neoplastic disease in an animal by administering to the animal an effective amount of a compound or salt selected from the group consisting of any one of the above embodiments of Formula XV, Formula XVI, Formula XVII, Formula XVIII, Formula XIX, and Formula XX.

This disclosure also provides compounds of the following Formula XXI:

FormulaXXI

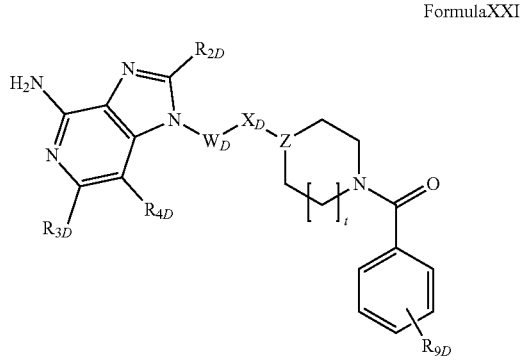

wherein $W_D$, $X_D$, $R_{2D}$, $R_{3D}$, $R_{4D}$, $R_{9D}$, Z and t are as defined below; and pharmaceutically acceptable salts thereof.

For compounds and salts, such as pharmaceutically acceptable salts, of Formula XXI: $R_{3D}$ and $R_{4D}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more $R_D$ groups.

$R_D$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$W_D$ is selected from the group consisting of a covalent bond, —O—, and —NH—;

$X_D$ is selected from the group consisting of alkylene, alkenylene, and alkynylene, wherein any of the alkylene, alkenylene, and alkynylene groups can be optionally interrupted by one or more —O— groups;

t is an integer from 0-4;

Z is —CH— or —N—;

$R_{9D}$ is -$Q_D$-N($R_{7D}$)—C(=N—$R_{5D}$)—N(H)$R_{6D}$;

$Q_D$ is selected from the group consisting of a covalent bond and alkylene;

$R_{2D}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{7D}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{5D}$ and $R_{6D}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XXI, $R_{3D}$ and $R_{4D}$ are taken together to form a fused benzene ring, a fused pyridine ring, or a fused cyclohexene ring.

In some embodiments of Formula XXI, $R_{3D}$ and $R_{4D}$ are taken together to form a fused benzene ring or a fused cyclohexene ring.

In some embodiments of Formula XXI, $R_{3D}$ and $R_{4D}$ are taken together to form a fused benzene ring or a fused pyridine ring.

In some embodiments of Formula XXI, $R_{3D}$ and $R_{4D}$ are taken together to form a fused benzene ring.

In some embodiments of Formula XXI, $R_{3D}$ and $R_{4D}$ are taken together to form a fused benzene ring, a fused pyridine ring, or a fused cyclohexene ring; wherein the fused benzene ring, fused pyridine ring, or fused cyclohexene ring is either unsubstituted or substituted by one and only one $R_D$ group.

In some embodiments of Formula XXI, $R_{3D}$ and $R_{4D}$ are taken together to form a fused benzene ring or a fused pyridine ring; wherein the fused benzene ring or fused pyridine ring is either unsubstituted or substituted by one and only one $R_D$ group.

In some embodiments of Formulas XXI, $R_D$ is selected from the group consisting of halogen, hydroxyl, alkyl, alkoxy, and haloalkyl.

In some embodiments of Formula XXI, t is 1.

In some embodiments of Formula XXI, t is 1and Z is —CH—.

In some embodiments of Formula XXI, $W_D$ is a covalent bond and $X_D$ is alkylene optionally interrupted by one or more —O— groups.

In some embodiments of Formula XXI, t is 1; Z is —CH—, $W_D$ is a covalent bond and $X_D$ is —CH$_2$—.

In some embodiments of Formula XXI, t is 1; Z is —CH—, $W_D$ is a covalent bond and $X_D$ is —CH$_2$CH$_2$—.

In some embodiments of Formula XXI, —$W_D$—$X_D$— is —O—C$_{2-7}$alkylene- or —C$_{2-8}$alkylene-.

In some embodiments of Formula XXI, —$W_D$—$X_D$— is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$CH$_2$—, —CH$_2$CH$_2$—O—CH$_2$CH$_2$—O—CH$_2$CH$_2$—, —(CH$_2$)$_{2-4}$—O—(CH$_2$)$_{2-4}$—, —(CH$_2$)$_{2-4}$—(OCH$_2$C$_2$CH$_2$—)$_{1-5}$, and —(CH$_2$)$_{2-6}$—(OCH$_2$C$_2$CH$_2$—)$_{1-4}$.

In some embodiments of Formula XXI, $R_{2D}$ is selected from the group consisting hydrogen, alkyl, alkoxyalkylenyl, alkylaminoalkylenyl, and hydroxyalkylenyl.

In some embodiments of Formulas XXI, $R_{2D}$ is selected from the group consisting hydrogen, alkyl, and alkoxyalkylenyl.

In some embodiments of Formula XXI, $R_{2D}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, —$CH_2CH_2OH$, and —$CH_2NHOCH_3$.

In some embodiments of Formula XXI, $R_{2D}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

In some embodiments of Formula XXI, $Q_D$ is selected from the group consisting of a covalent bond and $C_{1-4}$alkylene.

In some embodiments of Formulas XXI, $Q_D$ is selected from the group consisting of a covalent bond and $C_{1-2}$alkylene.

In some embodiments of Formulas XXI, $Q_D$ is selected from the group consisting of a covalent bond and —$CH_2$—.

In some embodiments of Formulas XXI, $Q_D$ is a covalent bond.

In some embodiments of Formula XXI, $R_{7D}$ is hydrogen, $C_{1-8}$alkyl, or —$CH_2Ph$.

In some embodiments of Formula XXI, $R_{7D}$ is hydrogen or $C_{1-4}$alkyl.

In some embodiments of Formula XXI, $R_{7D}$ is hydrogen.

In some embodiments of Formula XXI, $R_{7D}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_3$, —$CH_2CH_2CH(CH_3)_2$, cyclopentyl, -cyclohexyl, —$CH_2$(cyclopentyl), —$CH_2$(cyclohexyl), and —$CH_2CH_2$—O—$CH_3$.

In some embodiments of Formula XXI, $R_{7D}$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}$ Ph, wherein Ph can be either unsubstituted or substituted with one or more substituents selected from the group consisting of halogen, hydroxyl, alkyl, alkoxy, haloalkyl, and nitrile.

In some embodiments of Formula XXI, $R_{5D}$ and $R_{6D}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XXI, $R_{5D}$ and $R_{6D}$ are independently selected from the group consisting of hydrogen, alkyl, phenyl, and phenylalkylenyl.

In some embodiments of Formula XXI, $R_{5D}$ and $R_{6D}$ are independently selected from the group consisting of hydrogen, alkyl, cycloalkyl, cycloalkylalkylenyl, aryl, and arylalkylenyl.

In some embodiments of Formula XXI, $R_{5D}$ and $R_{6D}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$(CH_2)_{3-8}$—O—$CH_3$, —$CH_2CH_2OCH_3$, and —$CH_2CH_2CH_2N(CH_3)_2$.

In some embodiments of Formula XXI, $R_{5D}$ and $R_{6D}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

In some embodiments of Formula XXI, $R_{5D}$ and $R_{6D}$ are independently selected from the group consisting of hydrogen, —$C(O)OC(CH_3)_3$, and —$C(O)OCH_2Ph$.

In some embodiments of Formula XXI, $R_{5D}$ is hydrogen and $R_{6D}$ is hydrogen.

In some embodiments of Formula XXI, $R_{5D}$ is hydrogen, $R_{6D}$ is hydrogen and $R_{7D}$ is hydrogen.

In some embodiments of Formula XXI, $R_{5D}$ is alkyl and $R_{6D}$ is alkyl.

In some embodiments of Formula XXI I, $R_{5D}$ is $C_{1-8}$alkyl and $R_{6D}$ is $C_{1-8}$alkyl.

In some embodiments of Formula XXI, $R_{5D}$ is $C_{1-4}$ alkyl and $R_{6D}$ is $C_{1-4}$ alkyl.

In some embodiments of Formula XXI, $W_D$ is selected from the group consisting of a covalent bond and —O—; $X_D$ is alkylene optionally interrupted by one or more —O— groups; t is 1; Z is —CH—; $R_{2C}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

This disclosure also provides compounds of the following Formulas XXII-XXIII:

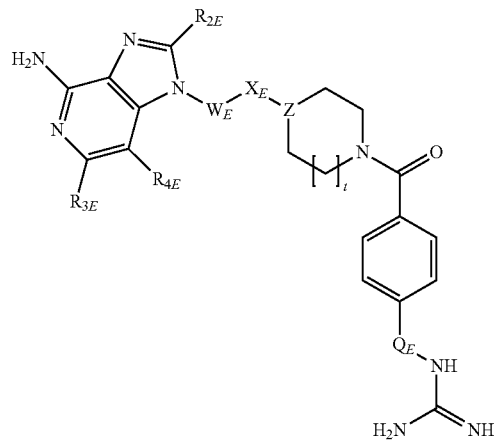

Formula XXII

Formula XXIII

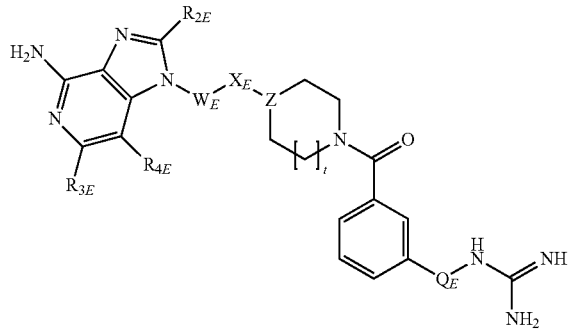

wherein $W_E$, $X_E$, $R_{2E}$, $R_{3E}$, $R_{4E}$, $Q_E$, Z and t are as defined below; and pharmaceutically acceptable salts thereof.

For compounds and salts, such as pharmaceutically acceptable salts, of Formulas XXII-XXIII: $R_{3E}$ and $R_{4E}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more $R_E$ groups.

$R_E$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$W_E$ is selected from the group consisting of a covalent bond, —O—, and —NH—;

$X_E$ is selected from the group consisting of alkylene, alkenylene, and alkynylene, wherein any of the alkylene, alkenylene, and alkynylene groups can be optionally interrupted by one or more —O— groups;

t is an integer from 0-4;

Z is —CH— or —N—;

$Q_E$ is selected from the group consisting of a covalent bond and alkylene;

$R_{2E}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl.

In some embodiments of Formulas XXII-XXIII, $R_{3E}$ and $R_{4E}$ are taken together to form a fused benzene ring, a fused pyridine ring, or a fused cyclohexene ring.

In some embodiments of Formulas XXII-XXIII, $R_{3E}$ and $R_{4E}$ are taken together to form a fused benzene ring or a fused cyclohexene ring.

In some embodiments of Formulas XXII-XXIII, $R_{3E}$ and $R_{4E}$ are taken together to form a fused benzene ring or a fused pyridine ring.

In some embodiments of Formulas XXII-XXIII, $R_{3E}$ and $R_{4E}$ are taken together to form a fused benzene ring.

In some embodiments of Formulas XXII-XXIII, $R_{3E}$ and $R_{4E}$ are taken together to form a fused benzene ring, a fused pyridine ring, or a fused cyclohexene ring; wherein the fused benzene ring, fused pyridine ring, or fused cyclohexene ring is either unsubstituted or substituted by one and only one $R_E$ group.

In some embodiments of Formulas XXII-XXIII, $R_{3E}$ and $R_{4E}$ are taken together to form a fused benzene ring or a fused pyridine ring; wherein the fused benzene ring or fused pyridine ring is either unsubstituted or substituted by one and only one $R_E$ group.

In some embodiments of Formulas XXII-XXIII, $R_E$ is selected from the group consisting of halogen, hydroxyl, alkyl, alkoxy, and haloalkyl.

In some embodiments of Formulas XXII-XXIII, t is 1.

In some embodiments of Formulas XXII-XXIII, t is 1 and Z is —CH—.

In some embodiments of Formulas XXII-XXIII, $W_E$ is a covalent bond and $X_E$ is alkylene optionally interrupted by one or more —O— groups.

In some embodiments of Formulas XXII-XXIII, Z is —CH—, and —$W_E$—$X_E$— is —O—$C_{1-7}$alkylene- or —$C_{1-8}$alkylene-.

In some embodiments of Formulas XXII-XXIII, —$W_E$—$X_E$— is selected from the group consisting of —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$CH$_2$—, —CH$_2$CH$_2$—O—CH$_2$CH$_2$—O—CH$_2$CH$_2$—, —(CH$_2$)$_{2-4}$—O—(CH$_2$)$_{2-4}$—, —(CH$_2$)$_{2-4}$—(OCH$_2$C$_2$CH$_2$—)$_{1-5}$, and —(CH$_2$)$_{2-6}$—(OCH$_2$CH$_2$—)$_{1-4}$.

In some embodiments of Formulas XXII-XXIII, $R_{2E}$ is selected from the group consisting hydrogen, alkyl, alkoxyalkylenyl, alkylaminoalkylenyl, and hydroxyalkylenyl.

In some embodiments of Formulas XXII-XXIII, $R_{2E}$ is selected from the group consisting hydrogen, alkyl, and alkoxyalkylenyl.

In some embodiments of Formulas XXII-XXIII, $R_{2E}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formulas XXII-XXIII, $R_{2E}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formulas XXII-XXIII, $Q_E$ is selected from the group consisting of a covalent bond and $C_{1-4}$alkylene.

In some embodiments of Formulas XXII-XXIII, $Q_E$ is selected from the group consisting of a covalent bond and $C_{1-2}$alkylene.

In some embodiments of Formulas XXII-XXIII, $Q_E$ is selected from the group consisting of a covalent bond and —CH$_2$—.

In some embodiments of Formulas XXII-XXIII, $Q_E$ is a covalent bond.

In some embodiments of Formulas XXII-XXIII, $W_E$ is selected from the group consisting of a covalent bond and —O—; $X_E$ is alkylene optionally interrupted by one or more —O— groups; t is 1; Z is —CH—; $R_{2E}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

This disclosure also provides compounds of the following Formula XXIV:

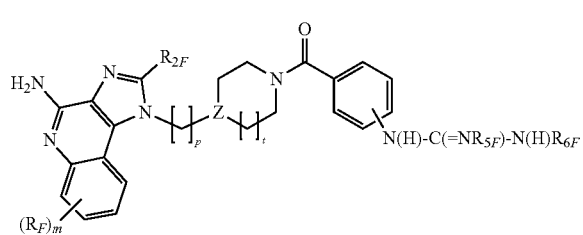

Formula XXIV wherein $R_F$, $R_{2F}$, $R_{5F}$, $R_{6F}$, Z, m, p, and t are defined for Formula XXIV below; and pharmaceutically acceptable salts thereof.

For the compounds of Formula XXIV:

m is an integer from 0 to 2;

p is an integer from 1 to 8;

t is an integer from 0-4;

Z is —CH— or —N—

$R_F$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$R_{2F}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{5F}$ and $R_{6F}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XXIV, m is 0 or 1.

In some embodiments of Formula XXIV, m is 0.

In some embodiments of Formula XXIV, p is an integer from 1 to 4.

In some embodiments of Formula XXIV, p is 1.

In some embodiments of Formula XXIV, t is 1

In some embodiments of Formula XXIV, t is 1 and Z is —CH—.

In some embodiments of Formula XXIV, t is 1 and Z is —N—.

In some embodiments of Formula XXIV, p is 1, t is 1, and Z is —CH—.

In some embodiments of Formula XXIV, p is 2, t is 1, and Z is —N—.

In some embodiments of Formula XXIV, $R_F$ is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.

In some embodiments of Formula XXIV, $R_F$ is selected from the group consisting of halogen, hydroxyl, alkyl, alkoxy, and haloalkyl.

In some embodiments of Formula XXIV, $R_{2F}$ is selected from the group consisting hydrogen, alkyl, alkoxyalkylenyl, alkylaminoalkylenyl, and hydroxyalkylenyl.

In some embodiments of Formula XXIV, $R_{2F}$ is selected from the group consisting hydrogen, alkyl, and alkoxyalkylenyl.

In some embodiments of Formula XXIV, $R_{2F}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formula XXIV, $R_{2F}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formula XXIV, $R_{2F}$ is —CH$_2$NHC(O)CH$_3$ or —CH$_2$NHC(O)cyclopropyl.

In some embodiments of Formula XXIV, $R_{2F}$ is —CH$_2$NHC(O)C$_{1-3}$alkyl.

In some embodiments of Formula XXIV, $R_{5F}$ and $R_{6F}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XXIV, $R_{5F}$ and $R_{6F}$ are independently selected from the group consisting of hydrogen, alkyl, phenyl, and phenylalkylenyl.

In some embodiments of Formula XXIV, $R_{5F}$ and $R_{6F}$ are independently selected from the group consisting of hydrogen, alkyl, cycloalkyl, cycloalkylalkylenyl, aryl, and arylalkylenyl.

In some embodiments of Formula XXIV, $R_{5F}$ and $R_{6F}$ are independently selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —(CH$_2$)$_{5-9}$CH$_3$, —CH$_2$CH$_2$CH(CH$_3$)$_2$, cyclopropyl, cyclopentyl, cyclohexyl, —CH$_2$-cyclopropyl, —CH$_2$-cyclopentyl, —CH$_2$-cyclohexyl, —CH$_2$CH$_2$OCH$_3$, —(CH$_2$)$_{3-8}$—O—CH$_3$, and —CH$_2$CH$_2$CH$_2$N(CH$_3$)$_2$.

In some embodiments of Formula XXIV, $R_{5F}$ and $R_{6F}$ are independently selected from the group consisting of hydrogen, alkyl, —CH$_2$Ph, —CH$_2$CH$_2$Ph, —CH$_2$CH$_2$—O-Ph, -Ph, —(CH$_2$)$_{3-8}$Ph, —(CH$_2$)$_{3-8}$—O-Ph, —CH$_2$CH$_2$—O—CH$_2$Ph, —(CH$_2$)$_{3-8}$—O—CH$_2$Ph, and —(CH$_2$)$_{2-8}$—O—(CH$_2$)$_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

In some embodiments of Formula XXIV, $R_{5F}$ and $R_{6F}$ are independently selected from the group consisting of hydrogen, —C(O)OC(CH$_3$)$_3$, and —C(O)OCH$_2$Ph.

In some embodiments of Formula XXIV, $R_{5F}$ hydrogen and $R_{6F}$ is hydrogen.

In some embodiments of Formula XXIV, $R_{5F}$ is alkyl and $R_{6F}$ is alkyl.

In some embodiments of Formula XXIV, $R_{5F}$ is $C_{1-8}$alkyl and $R_{6F}$ is $C_{1-8}$alkyl.

In some embodiments of Formula XXIV, $R_{5F}$ is $C_{1-4}$alkyl and $R_{6F}$ is $C_{1-4}$alkyl.

In some embodiments of Formula XXIV, the compound is present in the form of a salt. The salt is typically a pharmaceutically acceptable salt. Most commonly the salt is a hydrochloride or dihydrochloride salt.

The disclosure provides a method of inducing cytokine biosynthesis in an animal by administering to the animal an effective amount of a compound or salt selected from the group consisting of any one of the above embodiments of Formula XXI, Formula XXII, Formula XXIII, and Formula XXIV.

The disclosure also provides a method of inducing IFN-alpha biosynthesis in an animal by administering to the animal an effective amount of a compound or salt selected from any one of the above embodiments of Formula XXI, Formula XXII, Formula XXIII, and Formula XXIV.

The disclosure also provides a method of inducing IFN-gamma biosynthesis in an animal by administering to the animal an effective amount of a compound or salt selected from any one of the above embodiments of Formula XXI, Formula XXII, Formula XXIII, and Formula XXIV.

The disclosure also provides a method of inducing TNF-alpha biosynthesis in an animal by administering to the animal an effective amount of a compound or salt selected from any one of the above embodiments of Formula XXI, Formula XXII, Formula XXIII, and Formula XXIV.

The disclosure also provides a method of inducing IP-10 biosynthesis in an animal by administering to the animal an effective amount of a compound or salt selected from any one of the above embodiments of Formula XXI, Formula XXII, Formula XXIII, and Formula XXIV.

The disclosure also provides a method for treating a viral disease in an animal by administering to the animal an effective amount of a compound or salt selected from the group consisting of any one of the above embodiments of Formula XXI, Formula XXII, Formula XXIII, and Formula XXIV.

The disclosure also provides a method for treating a neoplastic disease in an animal by administering to the animal an effective amount of a compound or salt selected from the group consisting of any one of the above embodiments of Formula XXI, Formula XXII, Formula XXIII, and Formula XXIV.

The compounds of the disclosure may be synthesized by synthetic routes that include processes analogous to those well known in the chemical arts, particularly in light of the description contained herein. The starting materials are generally available from commercial sources such as Sigma-Aldrich Company (St. Louis, Mo.) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Compounds of the disclosure (Formulas I-XXIV) can be prepared using standard methods for synthesizing amide bonds. Compounds of Formulas I-XXIV can be prepared by reacting a primary or secondary amine of Formulas XXV-XXXIV with a guanidino substituted benzoic acid, such as for example 3-guanidinobenzoic acid, 4-guanidinobenzoic acid, and guanidinoalkylbenzoic acids (such as for example 4-guanidinomethylbenzoic acid, 3-guanidinomethylbenzoic acid, 4-(2-guanidinoethyl)benzoic acid, and 3-(2-guanidinoethyl)benzoic acid).

In one method, the compounds of Formulas I-XXIV can be prepared by using a coupling reagent such as DCC (1,3-dicyclohexylcarbodiimide) or EDCI (1-ethyl-3-(3-dimethylaminopropyl)carbodiimide hydrochloride) to form the amide bond between a guanidino substituted benzoic acid and an amine of Formulas XXV-XXXVI. In another method, the compounds of Formulas I-XXIV can be prepared by first converting a guanidino substituted benzoic acid to the corresponding acid chloride (for example by using SOCl$_2$) and then reacting the guanidino substituted benzoyl chloride with an amine of Formulas XXV-XXXIV. In yet another method, the compounds of Formulas I-XXIV can be prepared by first converting a guanidino substituted benzoic acid to an activated ester or anhydride (for example using a carboxylic acid activating agents such as N-hydroxy-5-norbornene-2,3-dicarboxyimide (HONB), N-hydroxysuccinimide (NHS), or isobutylchloroformate) and then reacting the activated compound with an amine of Formulas XXV-XXXIV.

General methods for preparing amides from the reaction of guanidino substituted benzoic acids and primary or secondary amines have been reported by Fisher in U.S. Pat. No. 5,731,324; Takada in U.S. Pat. No. 5,876,756; Chandrakumar in U.S. Pat. No. 5,773,646; Ueda in *Chemical Pharmaceutical Bulletin,* 41(8), pages 1387-1390; Sagi in *Bioorganic and Medicinal Chemistry* 13(5), pages 1487-1496; and Kitamura in the *Journal of Medicinal Chemistry,* 2001, 44, pages 2438-2450; all of which are incorporated herein by reference.

Several standard methods are known to those of ordinary skill in the art for preparing guanidino substituted benzoic acids from aminobenzoic acids and aminoalkylbenzoic acids. Reference for the preparation of such compounds are incorporated herein by reference and include: the synthesis of 3-guanidinobenzoic acid hydrochloride by reacting 3-aminobenzoic acid with 3,5-dimethylpyrazole-1-carboxamidine nitrate and diisopropylamine in dioxane/water which is reported in U.S. Pat. No. 5,773,646 (Chandrakumar); the synthesis of 4-guanidinomethylbenzoic acid by reacting 4-aminomethylbenzoic acid with S-methylisothiourea sulfate and 2M NaOH (aq) which is reported by Ueda in *Chemical Pharmaceutical Bulletin,* 41(8), pages 1387-1390; the synthesis of 4-guanidinobenzoic acid hydrochloride from 4-aminobenzoic acid which is reported in Example 64 of U.S. Pat. No. 5,731,324 (Fisher).

The syntheses of N,N'-bis-tert-butoxycarbonyl-4-guanidinobenzoic acid; N,N'-bis-tert-butoxycarbonyl-4-guanidinomethylbenzoic acid, and N,N'-bis-tert-butoxycarbonyl-4-(2-guanidinoethyl)benzoic acid are all reported by Kayser in *Bioorganic and Medicinal Chemistry Letters*, Volume 17

(2007), pages 2068-2073 (incorporated herein by reference). In each case the corresponding amino substituted benzoic acid was reacted with N,N'-bis(tert-butoxycarbonyl)-1H-pyrazole-1-carboxyamidine and trimethylamine in methanol.

In addition, 4-guanidinobenzoic acid hydrochloride [CAS number 42823-46-1] is commercially available from TCI America, Portland, Oreg.

General synthetic methods that are useful for the preparation of the intermediate amines of Formulas XXV-XXXIV have been previously described and many of the intermediate amine compounds are known compounds. References for the preparation of the intermediate amine compounds are incorporated by reference and include U.S. Pat. No. 7,799,800 (Wightman, see Example 1 Parts A-J), U.S. Pat. No. 7,115,622 (Crooks, see Reaction Schemes II, III, V and Examples 1-3,5, 67-69), U.S. Pat. No. 7,579,359 (Krepski, see Reaction Schemes VI and VII), U.S. Patent Application Publication No. 2013/0230578 (Wightman, see Example 1 Parts A-D), U.S. Pat. No. 7,163,947 (Griesgraber, see Scheme VII and Example 14 Parts A-F), U.S. Pat. No. 6,069,149 (Nanba, see Examples 5, 10, 12, 17, 20-21, 28, 33, 39), U.S. Pat. No. 8,728,486 (David, see Compound 7c and 7d), U.S. Pat. No. 7,968,563 (Kshirsagar), U.S. Pat. No. 8,088,790 (Kshirsagar, see Scheme IV, Example 8 Parts A-D, Example 56 Parts A-D, Example 62 Parts A-E), U.S. Pat. No. 8,168,802 (Hays), U.S. Pat. No. 9,034,336 (Ferguson), U.S. Pat. No. 7,884,207 (Stoermer, see Scheme VII, Example 286 Parts A-B, Example 339 Parts A-D).

Some examples of intermediate amine compounds that can be converted into the guanidine substituted benzamides of the disclosure (Formulas I-XXIV) are shown in Formulas XXV-XXXIV, wherein $R_2$, $R_{2A}$, $R_{2B}$, $R_{2D}$, $R_3$, $R_{3D}$, $R_4$, $R_{4D}$, $R_8$, $R_{8B}$, $R_A$, W, $W_B$, $W_D$, X, $X_B$, $X_D$, Z, m, J, K, can be as defined in any of the embodiments above.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in T. W. Greene and P. G. M. Wuts, *Protective Groups in Organic Synthesis*, John Wiley & Sons, New York, USA, 1991.

Conventional methods and techniques of separation and purification can be used to isolate the IRM compounds used in the formulations of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

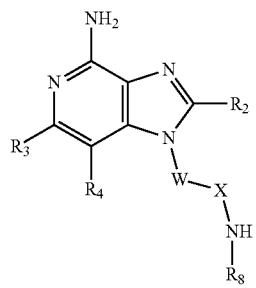

Formula XXV

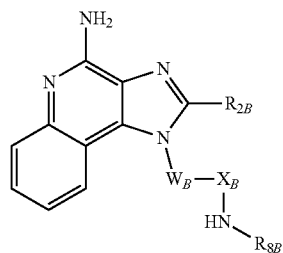

Formula XXVI

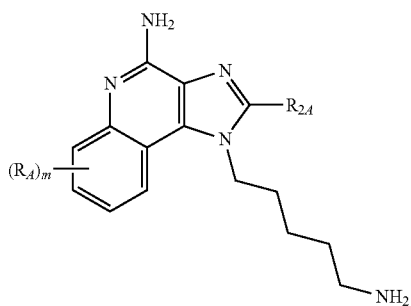

Formula XVII

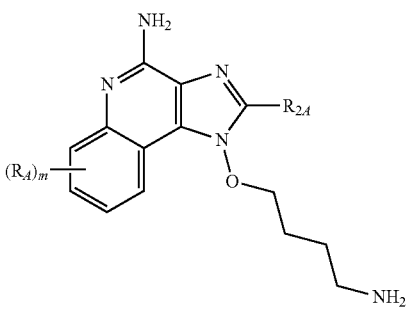

Formula XVIII

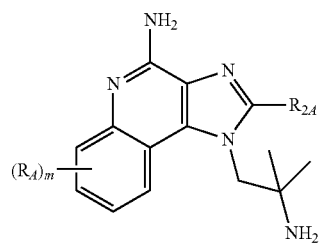

Formula XXIX

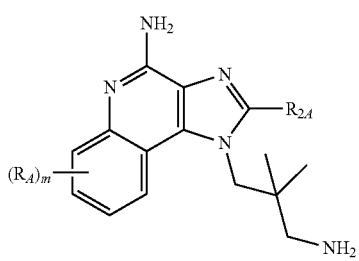

Formula XXX

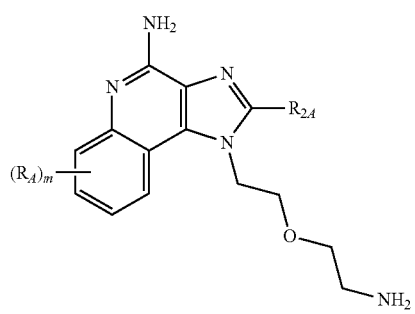

Formula XXXI

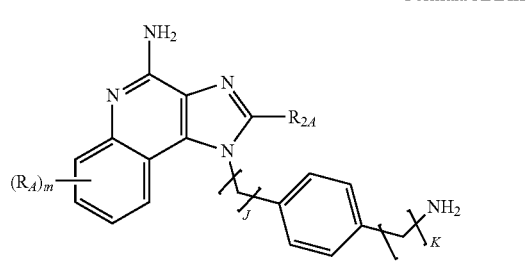

Formula XXXII

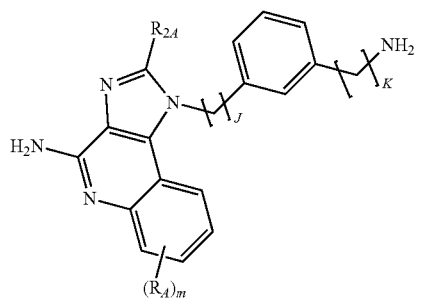

Formula XXXIII

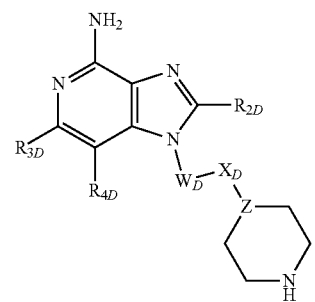

Formula XXXIV

When a group (or substituent or variable) is present more than once in any Formula described herein, each group (or substituent or variable) is independently selected, whether explicitly stated or not. For example, for a Formula containing "—X-arylene-X-" each "X" group is independently selected.

For simplicity and convenience, it is understood that some of the compounds of the disclosure may be drawn in a certain isomeric form, but in fact all stereoisomers [i.e. configurational isomers (e.g. E,Z isomers), conformational isomers (e.g. rotational isomers), diastereomers, enantiomers] are expressly included within the scope of this disclosure (whether explicitly drawn or not).

Specifically, it is understood that for compounds of Formulas I-XIV, all stereoisomers [i.e. configurational isomers (e.g. E,Z isomers), conformational isomers (e.g. rotational isomers), diastereomers, enantiomers] are expressly included (whether explicitly drawn or not).

Compounds or salts of the present disclosure may exist in different tautomeric forms, and it is understood that all such forms are expressly included within the scope of this disclosure. Prodrugs of the disclosed compounds can also be prepared by attaching to the compounds a functional group that can be cleaved under physiological conditions. Typically, a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella. "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

For any of the compounds of Formula I presented herein, each one of the variables R, $R_2$, $R_3$, $R_4$, $R_5$, $R_6$, $R_7$, $R_8$, $R_9$, Q, W, X, Z, q, t in any of the Formula I embodiments can be combined with any one or more of the other variables in any of the Formula I embodiments, as would be understood by one of ordinary skill in the art. Each of the resulting combinations of variables is also an embodiment of the disclosure.

For any of the compounds of Formulas II-V presented herein, each one of the variables R, $R_2$, $R_5$, $R_6$, $R_7$, $R_8$, n, Q, W, X in any of the Formula II-V embodiments can be combined with any one or more of the other variables in any of the Formula II-V embodiments, as would be understood by one of ordinary skill in the art. Each of the resulting combinations of variables is also an embodiment of the disclosure.

For any of the compounds of Formulas VI-X presented herein, each one of the variables $R_A$, $R_{2A}$, $R_{5A}$, $R_{6A}$, m in any of the Formula VI-X embodiments can be combined with any one or more of the other variables in any of the Formula VI-X embodiments, as would be understood by one of ordinary skill in the art. Each of the resulting combinations of variables is also an embodiment of the disclosure.

For any of the compounds of Formulas XI-XII presented herein, each one of the variables $R_A$, $R_{2A}$, $R_{5A}$, $R_{6A}$, m, J, K in any of the Formulas XI-XII embodiments can be combined with any one or more of the other variables in any of the Formulas XI-XII embodiments, as would be understood by one of ordinary skill in the art. Each of the resulting combinations of variables is also an embodiment of the disclosure.

For any of the compounds of Formula XIII presented herein, each one of the variables $R_A$, $R_{2A}$, $R_{5A}$, $R_{6A}$, m, L in any of the Formula XIII embodiments can be combined with any one or more of the other variables in any of the Formula XIII embodiments, as would be understood by one of ordinary skill in the art. Each of the resulting combinations of variables is also an embodiment of the disclosure.

For any of the compounds of Formula XIV presented herein, each one of the variables, $R_{2B}$, $R_{5B}$, $R_{6B}$, $R_{7B}$, $R_{8B}$, $R_{9B}$, $Q_B$, $W_B$, $X_B$ in any of the Formula XIV embodiments can be combined with any one or more of the other variables in any of the Formula XIV embodiments, as would be understood by one of ordinary skill in the art. Each of the resulting combinations of variables is also an embodiment of the disclosure.

For any of the compounds of Formulas XV-XVI presented herein, each one of the variables $R_C$, $R_{2C}$, $R_{3C}$, $R_{4C}$, $R_{8C}$, $W_C$, $X_C$, $Q_C$ in any of the Formulas XV-XVI embodiments can be combined with any one or more of the other variables in any of the Formulas XV-XVI embodiments, as would be understood by one of ordinary skill in the art. Each of the resulting combinations of variables is also an embodiment of the disclosure.

For any of the compounds of Formulas XVII-XVIII presented herein, each one of the variables $R_C$, $R_{2C}$, $R_{3C}$, $R_{4C}$, $R_{8C}$, $W_C$, $X_C$ in any of the Formulas XVII-XVIII embodiments can be combined with any one or more of the other variables in any of the Formulas XVII-XVIII embodiments, as would be understood by one of ordinary skill in the art. Each of the resulting combinations of variables is also an embodiment of the disclosure.

For any of the compounds of Formulas XIX-XX presented herein, each one of the variables $R_{2C}$, $R_{8C}$, $W_C$, $X_C$, $Q_C$ in any of the Formulas XIX-XX embodiments can be combined with any one or more of the other variables in any of the Formulas XIX-XX embodiments, as would be understood by one of ordinary skill in the art. Each of the resulting combinations of variables is also an embodiment of the disclosure.

In an embodiment, 4-amino-imidazo[4,5-c]quinolone compounds are disclosed that contain a guanidine substituted benzamide group. The guanidine substituted benzamide moiety is attached at the N-1 position of the imidazo [4,5-c]quinolone ring via a first linker group (such as a $C_{1-10}$ alkylene that is optionally interrupted by one or more —O— groups). The guanidine substituted benzamide is attached to the first linker by a covalent bond with amide nitrogen.

The guanidine group is attached to the benzamide at either the ortho, meta, or para position of the benzene ring (preferably at the meta or para position). The guanidine group is covalently bonded directly to the benzene ring of the benzamide moiety or it is attached to the benzene ring via a second linker group. A suitable second linker group is a $C_{1-8}$ alkylene that is optionally interrupted with one or more —O— groups.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The exact amount of compound or salt used in a pharmaceutical composition of the disclosure will vary according to factors known to those of skill in the art, such as the physical and chemical nature of the compound or salt, the nature of the carrier, and the intended dosing regimen.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the compositions of the disclosure will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In some embodiments, the compositions of the disclosure will contain sufficient active ingredient or prodrug to provide a dose of for example, from about 0.01 mg/m² to about 5.0 mg/m², computed according to the Dubois method, in which the body surface area of a subject (m²) is computed using the subject's body weight: $m^2=(wt\ kg^{0.425} \times height\ cm^{0.725}) \times 0.007184$, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used to administer the compounds or salts of the disclosure to an animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with one another or with other active agents, including additional immune response modifiers, antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure or salts are useful for activating the immune response in a number of different ways, rendering them useful in the treatment of a variety of disorders. As such, the compounds or salts of the disclosure (compounds or salts of Formulas I-XXIV) are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure (Formulas I-XVIII) induce cytokine production is through the activation of Toll-like receptors (TLRs) in the immune system, particularly TLR-7 and/or TLR-8, however other mechanisms may be involved. It is believed that in the immune system pathways (i.e. mechanisms) for cytokine induction, the compounds or salts of the disclosure (Formulas I-XVIII) primarily act as agonists of TLR-7 and/or TLR-8, however other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in an animal by administering an effective amount of a compound or salt of the disclosure to the animal. The animal to which the compound or salt is administered for induction of cytokine production may have one or more diseases, disorders, or conditions described below, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus, avian influenza), a paramyxovirus (e.g., parainfluenzavirus, mumps virus, measles virus, and respiratory syncytial virus (RSV), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), ebolavirus;

Neoplastic diseases such as bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such a atopic dermatitis or eczema, eosinophilia, asthma, allergy, allergic rhinitis, and Ommen's syndrome;

Diseases associated with wound repair, such as, for example, inhibition of keloid formation and other types of scarring (e.g., enhancing wound healing, including chronic wounds);

Parasitic diseases including but not limited to malaria, leishmaniasis, cryptosporidiosis, toxoplasmosis, and trypanosome infection.

In addition, a compound, salt, or composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, haepatitis A vaccine, hepatitis B vaccine, hepatitis C vaccine, influenza A vaccine, influenza B vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or compositions identified herein may be particularly useful as vaccine adjuvants when used in conjunction with tumor antigens associated with colorectal cancer, head and neck cancer, breast cancer, lung cancer and melanoma.

Compounds, salts, or compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in an animal in need thereof (having the disease) by administering a therapeutically effective amount of a compound, salt, or composition to the animal.

An animal may also be vaccinated by administering an effective amount of a compound, salt, or composition described herein as a vaccine adjuvant. In one embodiment, a method of vaccinating an animal includes administering an effective amount of a compound, salt, or composition described herein to the animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds or salts or compositions identified herein may be particularly useful when an effective amount is administered to an animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e. applied directly to the surface of a tumor, a lesion, a wart, or an infected tissue, etc.).

In one embodiment an effective amount of compound, salt, or composition described herein, such as an aqueous composition is administered into the bladder of an animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of about 100 ng/kg to about 50 mg/kg, preferably about 10μ/kg to about 5 mg/kg. In other embodiments, the amount can be, for example, from about 0.01 mg/m$^2$ to about 5.0 mg/m$^2$, (computed according to the Dubois method as described above) although in other embodiments the induction of cytokine biosynthesis may be performed by administering a compound or salt in a dose outside this range. In some of these embodiments, the method includes administering sufficient compound or salt or composition to provide a dose from about 0.1 mg/m² to about 2.0 mg/m² to the subject, for example, a dose of from about 0.4 mg/m² to about 1.2 mg/m².

A method of treating a viral infection in an animal and a method of treating a neoplastic disease in an animal can include administering an effective amount of at least one compound or salt described herein to the animal. An effective amount to treat or inhibit a viral infection can be an amount that will cause a reduction in one or more of the manifestations of viral infection, such as viral lesions, viral load, rate of virus production, and mortality as compared to untreated control animals. The precise amount that is effective for such treatment will vary according to factors known in the art but it is normally a dose of about 100 ng/kg to about 50 mg/kg, preferably about 10 µg/kg to about 5 mg/kg. An amount of a compound or salt effective to treat a neoplastic condition can be an amount that causes a reduction in tumor size or in the number of tumor foci. The precise amount will vary according to factors known in the art but is typically about 100 ng/kg to about 50 mg/kg, preferably about 10 µg/kg to about 5 mg/kg. In other embodiments, the amount is typically, for example, from about 0.01 mg/m² to about 5.0 mg/m², (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose from about 0.1 mg/m² to about 2.0 mg/m² to the subject, for example, a dose of from about 0.4 mg/m² to about 1.2 mg/m².

EMBODIMENTS

Embodiment 1 is a compound of Formula (I):

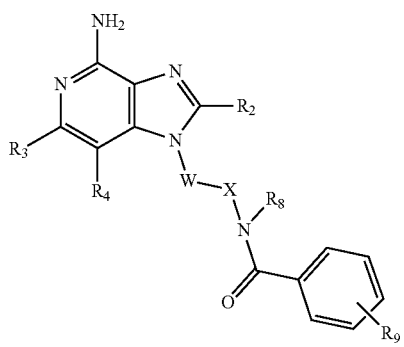

Formula I wherein:

$R_3$ and $R_4$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;

R is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

W is selected from the group consisting of a covalent bond, —O—, and —NH—;

X is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

$R_9$ is -Q-N($R_7$)—C(=N—$R_5$)—N(H)$R_6$;

Q is selected from the group consisting of a covalent bond and alkylene;

$R_2$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_8$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_7$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxyl, alkoxy, alkyl, haloalkyl, and nitrile;

$R_5$ and $R_6$ are independently selected from the group consisting of hydrogen, —C(O)—O— alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and enzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; or a pharmaceutically acceptable salt thereof.

Embodiment 2 is the compound or salt of embodiment 1, wherein $R_3$ and $R_4$ are taken together to form a fused benzene ring, a fused pyridine ring, or a fused cyclohexene ring.

Embodiment 3 is the compound or salt of any one of the embodiments 1-2, wherein $R_3$ and $R_4$ are taken together to form a fused benzene ring, a fused pyridine ring, or a fused cyclohexene ring, and wherein the fused benzene ring, fused pyridine ring, or fused cyclohexene ring is either unsubstituted or substituted by one and only one R group.

Embodiment 4 is the compound or salt of any one of the embodiments 1-3, wherein $R_3$ and $R_4$ are taken together to form a fused benzene ring or a fused cyclohexene ring, and wherein the fused benzene ring, or fused cyclohexene ring is either unsubstituted or substituted by one and only one R group.

Embodiment 5 is the compound or salt of any one of the embodiments 1-3, wherein $R_3$ and $R_4$ are taken together to form a fused benzene ring or a fused pyridine ring, and wherein the fused benzene ring, or fused pyridine ring is either unsubstituted or substituted by one and only one R group.

Embodiment 6 is the compound or salt of any one of the embodiments 1-5, wherein R is selected from the group consisting of hydroxyl, F, Cl, —CF$_3$, —OCF$_3$, —O—C$_{1-6}$ alkyl, and —C$_{1-6}$alkyl.

Embodiment 7 is the compound or salt of any one of the embodiments 1-5, wherein R is selected from the group consisting of hydroxyl, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

Embodiment 8 is the compound or salt of any one of the embodiments 1-5, wherein R is —C(O)OC$_{1-4}$ alkyl.

Embodiment 9 is the compound or salt of any one of the embodiments 1-5, wherein R is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

Embodiment 10 is the compound or salt of any one of the embodiments 1-9, wherein $R_7$ is hydrogen, alkyl, or —CH$_2$Ph.

Embodiment 11 is the compound or salt of any one of the embodiments 1-10, wherein $R_7$ is hydrogen, C$_{1-8}$ alkyl, or —CH$_2$Ph.

Embodiment 12 is the compound or salt of any one of the embodiments 1-11, wherein $R_7$ is hydrogen or C$_{1-4}$ alkyl.

Embodiment 13 is the compound or salt of any one of the embodiments 1-9, wherein $R_7$ is selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$CH$_2$CH(CH$_3$)$_2$, cyclopentyl, cyclohexyl, —CH$_2$(cyclopentyl), —CH$_2$(cyclohexyl), and —CH$_2$CH$_2$—O—CH$_3$.

Embodiment 14 is the compound or salt of any one of the embodiments 1-9, wherein $R_7$ is selected from the group consisting of hydrogen, alkyl, —CH$_2$Ph, —CH$_2$CH$_2$Ph, —CH$_2$CH$_2$—O-Ph, —CH$_2$CH$_2$—O—CH$_2$Ph, and —(CH$_2$)$_{2-6}$—O—(CH$_2$)$_{1-6}$ Ph, wherein Ph can be either unsubstituted or substituted with one or more substituents independently selected from the group consisting of halogen, hydroxyl, alkyl, alkoxy, haloalkyl, and nitrile.

Embodiment 15 is the compound or salt of any one of the embodiments 1-14, wherein $R_7$ is hydrogen.

Embodiment 16 is the compound or salt of any of the embodiments 1-14 wherein $R_7$ is alkyl.

Embodiment 17 is the compound or salt of any one of the embodiments 1-16, wherein W is a covalent bond or —O—.

Embodiment 18 is the compound or salt of any one of the embodiments 1-17, wherein X is alkylene optionally interrupted by one or more —O— groups.

Embodiment 19 is the compound or salt of any one of the embodiments 1-17, wherein X is selected from the group consisting of —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$CH$_2$—, —CH$_2$CH$_2$—O—CH$_2$CH$_2$—O—CH$_2$CH$_2$—, —(CH$_2$)$_{2-4}$—O—(CH$_2$)$_{2-4}$—, —(CH$_2$)$_{2-4}$—(OCH$_2$C$_2$CH$_2$—)$_{1-5}$, and —(CH$_2$)$_{2-6}$—(OCH$_2$C$_2$CH$_2$—)$_{1-4}$.

Embodiment 20 is the compound or salt of any one of the embodiments 1-18, wherein X is —C$_{1-5}$alkylene-arylene-C$_{1-5}$alkylene- or —C$_{1-5}$alkylene-heteroarylene-C$_{1-5}$alkylene-.

Embodiment 21 is the compound or salt of any of the embodiments 1-19, wherein X is —CH$_2$-phenylene-CH$_2$—.

Embodiment 22 is the compound or salt of any of the embodiments 1-21, wherein Q is a covalent bond or C$_{1-4}$alkylene.

Embodiment 23 is the compound or salt of any of the embodiments 1-22, wherein Q is selected from the group consisting of a covalent bond, —CH$_2$—, —CH$_2$CH$_2$—, —CH$_2$CH$_2$CH$_2$—, and —CH$_2$CH$_2$CH$_2$CH$_2$—.

Embodiment 24 is the compound or salt of any of the embodiments 1-23, wherein Q is selected from the group consisting of a covalent bond or —CH$_2$—.

Embodiment 25 is the compound or salt of any of the embodiments 1-24, wherein Q is a covalent bond.

Embodiment 26 is the compound or salt of any of the embodiments 1-25, wherein $R_8$ is selected from the group consisting of hydrogen, alkyl, and arylalkylenyl.

Embodiment 27 is the compound or salt of any of the embodiments 1-26, wherein $R_8$ is hydrogen.

Embodiment 28 is the compound or salt of any one of the embodiments 1-27, wherein $R_2$ is selected from the group consisting hydrogen, alkyl, alkoxyalkylenyl, alkylaminoalkylenyl, and hydroxyalkylenyl.

Embodiment 29 is the compound or salt of any one of the embodiments 1-28, wherein $R_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, and —CH$_2$CH$_2$OH.

Embodiment 30 is the compound or salt of any one of the embodiments 1-29, wherein $R_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 31 is the compound or salt of any one of the embodiments 1-28, wherein $R_2$ is —CH$_2$NHOCH$_3$, —CH$_2$NHC(O)CH$_3$ or —CH$_2$NHC(O)cyclopropyl.

Embodiment 32 is the compound or salt of any one of the embodiments 1-31, wherein $R_5$ and $R_6$ are independently selected from the group consisting of hydrogen, alkyl, phenyl, and phenylalkylenyl.

Embodiment 33 is the compound or salt of any one of the embodiments 1-31, wherein $R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 34 is the compound or salt of any one of the embodiments 1-31, wherein $R_5$ and $R_6$ are independently selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —(CH$_2$)$_{5-9}$CH$_3$, —CH$_2$CH$_2$CH (CH$_3$)$_2$, cyclopropyl, cyclopentyl, cyclohexyl, —CH$_2$-cyclopropyl, —CH$_2$-cyclopentyl, —CH$_2$-cyclohexyl, —CH$_2$CH$_2$—O—CH$_3$, —(CH$_2$)$_{3-8}$—O—CH$_3$, and —CH$_2$CH$_2$CH$_2$N(CH$_3$)$_2$.

Embodiment 35 is the compound or salt of any one of the embodiments 1-31, wherein R$_5$ and R$_6$ are independently selected from the group consisting of hydrogen, alkyl, —CH$_2$Ph, —CH$_2$CH$_2$Ph, —CH$_2$CH$_2$—O-Ph, -Ph, —(CH$_2$)$_{3-8}$Ph, —(CH$_2$)$_{3-8}$—O-Ph, —CH$_2$CH$_2$—O—CH$_2$Ph, —(CH$_2$)$_{3-8}$—O—CH$_2$Ph, and —(CH$_2$)$_{2-8}$—O—(CH$_2$)$_{1-4}$Ph, wherein the Ph group can be either unsubstituted or substituted with one or more substituents independently selected from the group consisting of halogen, hydroxyl, alkoxy, alkyl, haloalkyl, cycloalkyl, and nitrile.

Embodiment 36 is the compound or salt of any one of the embodiments 31, wherein R$_5$ and R$_6$ are both hydrogen.

Embodiment 37 is the compound or salt of any one of the embodiments 1-36, wherein the pharmaceutically acceptable salt is hydrochloride.

Embodiment 38 is the compound or salt of any one of the embodiments 1-36, wherein the pharmaceutically acceptable salt is dihydrochloride.

Embodiment 39 is a compound of Formula XIV:

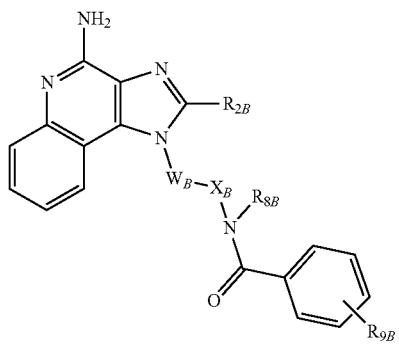

Formula XIV wherein:

W$_B$ is selected from the group consisting of a covalent bond, —O—, and —NH—;

X$_B$ is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

R$_{9B}$ is -Q$_B$-N(R$_{7B}$)—C(=N—R$_{5B}$)—N(H)R$_{6B}$;

Q$_B$ is selected from the group consisting of a covalent bond and alkylene;

R$_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

R$_{8B}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

R$_{7B}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxyl, alkoxy, alkyl, haloalkyl, and nitrile;

R$_{5B}$ and R$_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino;

or a pharmaceutically acceptable salt thereof.

Embodiment 40 is the compound or salt of embodiment 39, wherein R$_{7B}$ is hydrogen, alkyl, or —CH$_2$Ph.

Embodiment 41 is the compound or salt of any one of the embodiments 39-40, wherein R$_{7B}$ is hydrogen, C$_{1-8}$ alkyl, or —CH$_2$Ph.

Embodiment 42 is the compound or salt of any one of the embodiments 39-41, wherein R$_{7B}$ is hydrogen or C$_{1-4}$ alkyl.

Embodiment 43 is the compound or salt of embodiment 39, wherein R$_{7B}$ is selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$CH$_2$CH(CH$_3$)$_2$, cyclopentyl, cyclohexyl, —CH$_2$(cyclopentyl), —CH$_2$(cyclohexyl), and —CH$_2$CH$_2$—O—CH$_3$.

Embodiment 44 is the compound or salt of embodiment 39, wherein R$_{7B}$ is selected from the group consisting of hydrogen, alkyl, —CH$_2$Ph, —CH$_2$CH$_2$Ph, —CH$_2$CH$_2$—O-Ph, —CH$_2$CH$_2$—O—CH$_2$Ph, and —(CH$_2$)$_{2-6}$—O—(CH$_2$)$_{1-6}$Ph, wherein Ph can be either unsubstituted or substituted with one or more substituents independently selected from the group consisting of halogen, hydroxyl, alkyl, alkoxy, and, nitrile.

Embodiment 45 is the compound or salt of embodiments 39-44, wherein X$_B$ is alkylene optionally interrupted with one or more —O—.

Embodiment 46 is the compound or salt of any one of the embodiments 39-45, X$_B$ is alkylene.

Embodiment 47 is the compound or salt of any one of the embodiments 39-46, wherein X$_B$ is selected from the group consisting of —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$CH$_2$—, —CH$_2$CH$_2$—O—CH$_2$CH$_2$—O—CH$_2$CH$_2$—, —(CH$_2$)$_{2-4}$—O—(CH$_2$)$_{2-4}$—, —(CH$_2$)$_{2-4}$—(OCH$_2$C$_2$CH$_2$—)$_{1-5}$, and —(CH$_2$)$_{2-6}$—(OCH$_2$C$_2$CH$_2$—)$_{1-4}$.

Embodiment 48 is the compound or salt of any one of the embodiments 39-45, wherein $X_B$ is —$C_{1-5}$alkylene-arylene-$C_{1-5}$alkylene- or —$C_{1-5}$alkylene-heteroarylene-$C_{1-5}$alkylene-.

Embodiment 49 is the compound or salt of any one of the embodiments 39-45, wherein $X_B$ is —$CH_2$-phenylene-$CH_2$—.

Embodiment 50 is the compound or salt of any one of the embodiments 39-49, wherein $R_{2B}$ is selected from the group consisting hydrogen, alkyl, alkoxyalkylenyl, alkylaminoalkylenyl, and hydroxyalkylenyl.

Embodiment 51 is the compound or salt of any one of the embodiments 39-50, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, and —$CH_2CH_2OH$.

Embodiment 52 is the compound or salt of any one of the embodiments 39-51, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

Embodiment 53 is the compound or salt of embodiment 39, wherein $R_{2B}$ is —$CH_2NHOCH_3$, —$CH_2NHC(O)CH_3$ or —$CH_2NHC(O)$cyclopropyl.

Embodiment 54 is the compound or salt of any of the embodiments 39-53, wherein $Q_B$ is a covalent bond or $C_{1-4}$alkylene.

Embodiment 55 is the compound or salt of any one of the embodiments 39-54, wherein $Q_B$ is selected from the group consisting of a covalent bond, —$CH_2$—, —$CH_2CH_2$—, —$CH_2CH_2CH_2$—, and —$CH_2CH_2CH_2CH_2$—.

Embodiment 56 is the compound or salt of any one of the embodiments 39-55, wherein $Q_B$ is selected from the group consisting of a covalent bond or —$CH_2$—.

Embodiment 57 is the compound or salt of any one of the embodiments 39-55, wherein $Q_B$ is a covalent bond.

Embodiment 58 is the compound or salt of any one of the embodiments 39-57, wherein $R_{8B}$ is selected from the group consisting of hydrogen, alkyl, and arylalkylenyl.

Embodiment 59 is the compound or salt of any one of the embodiments 39-58, wherein $R_{8B}$ is hydrogen.

Embodiment 60 is the compound or salt of any one of the embodiments 39-59, wherein $R_{5B}$ and $R_{6B}$ are independently selected from the group consisting of hydrogen, alkyl, phenyl, and phenylalkylenyl.

Embodiment 61 is the compound or salt of any one of the embodiments 39-60, wherein $R_{5B}$ and $R_{6B}$ are independently selected from the group consisting of hydrogen, alkyl, phenyl, and phenylalkylenyl.

Embodiment 62 is the compound or salt of any one of the embodiments 39-61, wherein $R_{5B}$ is alkyl and $R_{6B}$ is alkyl.

Embodiment 63 is the compound or salt of any one of the embodiments 39-59, wherein $R_{5B}$ and $R_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 64 is the compound or salt of any one of the embodiments 39-59, wherein $R_{5B}$ and $R_{6B}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}$ $CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$.

Embodiment 65 is the compound or salt of any one of the embodiments 39-59, wherein $R_{5B}$ and $R_{6B}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}$ Ph, wherein the Ph group can be either unsubstituted or substituted with one or more substituents independently selected from the group consisting of halogen, hydroxyl, alkoxy, alkyl, haloalkyl, cycloalkyl, and nitrile.

Embodiment 66 is the compound or salt of any one of the embodiments 39-65, wherein the pharmaceutically acceptable salt is hydrochloride.

Embodiment 67 is the compound or salt of any one of the embodiments 39-65, wherein the pharmaceutically acceptable salt is dihydrochloride.

Embodiment 68 is a method of inducing biosynthesis of IFN-alpha in an animal comprising administering an effective amount of a compound or salt of any one of the embodiments 1-67 to the animal.

Embodiment 69 is a method of inducing biosynthesis of IFN-gamma in an animal comprising administering an effective amount of a compound or salt of any one of the embodiments 1-67 to the animal.

Embodiment 70 is a method of inducing biosynthesis of TNF-alpha in an animal comprising administering an effective amount of a compound or salt of any one of the embodiments 1-67 to the animal.

Embodiment 71 is a method of inducing biosynthesis of IP-10 in an animal comprising administering an effective amount of a compound or salt of any one of the embodiments 1-67 to the animal.

Embodiment 72 is a method of inducing cytokine biosynthesis in an animal comprising administering an effective amount of a compound or salt of any one of the embodiments 1-67 to the animal.

Embodiment 73 is a pharmaceutical composition comprising a therapeutically effective amount of a compound or salt of embodiment 1 in combination with a pharmaceutically acceptable carrier.

Embodiment 74 is a pharmaceutical composition comprising a therapeutically effective amount of a compound or salt of any one of the embodiments 1-67 in combination with a pharmaceutically acceptable carrier.

Embodiment 75 is a compound of Formula XV or Formula XVI:

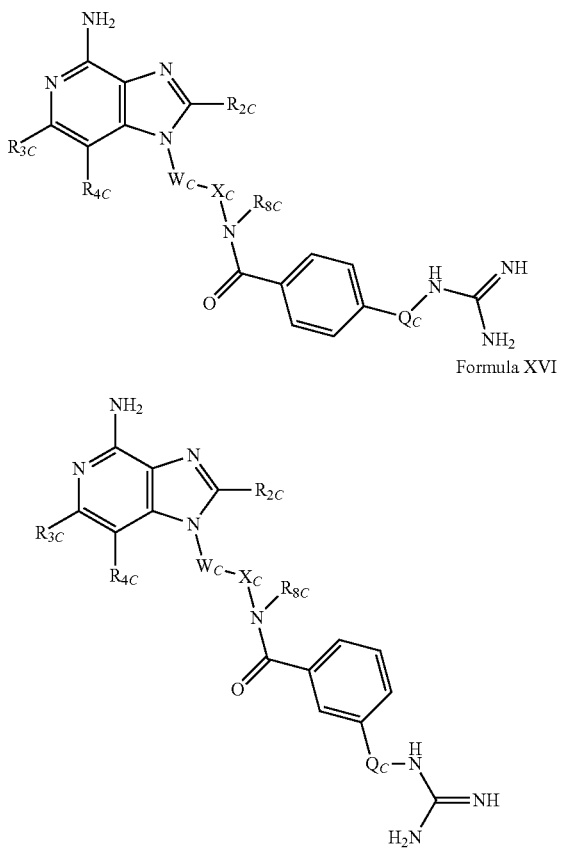

Formula XV

Formula XVI wherein:

R$_{3C}$ and R$_{4C}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R$_C$ groups;

R$_C$ is selected from the group consisting of halogen, hydroxyl, alkyl, alkoxy, haloalkylenyl, —C(O)—O-alkyl, —C(O)—OCH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

W$_C$ is selected from the group consisting of a covalent bond, —O—, and —NH—;

X$_C$ is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

R$_{2C}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

Q$_C$ is selected from the group consisting of a covalent bond and alkylene;

R$_{2C}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

R$_{8C}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

or a pharmaceutically acceptable salt thereof.

Embodiment 76 is the compound or salt of embodiment 75, wherein R$_{3C}$ and R$_{4C}$ are taken together to form a fused benzene ring, a fused pyridine ring, or a fused cyclohexene ring.

Embodiment 77 is the compound or salt of any one of the embodiments 75-76, wherein R$_{3C}$ and R$_{4C}$ are taken together to form a fused benzene ring, a fused pyridine ring, or a fused cyclohexene ring, and wherein the fused benzene ring, fused pyridine ring, or fused cyclohexene ring is either unsubstituted or substituted by one and only one R$_C$ group.

Embodiment 78 is the compound or salt of any one of the embodiments 75-77, wherein R$_{3C}$ and R$_{4C}$ are taken together to form a fused benzene ring or a fused cyclohexene ring, and wherein the fused benzene ring, or fused cyclohexene ring is either unsubstituted or substituted by one and only one R$_C$ group.

Embodiment 79 is the compound or salt of any one of the embodiments 75-77, wherein R$_{3C}$ and R$_{4C}$ are taken together to form a fused benzene ring or a fused pyridine ring, and wherein the fused benzene ring, or fused pyridine ring is either unsubstituted or substituted by one and only one R$_C$ group.

Embodiment 80 is the compound or salt of any one of the embodiments 75-79, wherein R$_{3C}$ and R$_{4C}$ are taken together to form a fused benzene ring that is unsubstituted.

Embodiment 81 is the compound or salt of any one of the embodiments 75-80, wherein R$_C$ is selected from the group consisting of hydroxyl, F, Cl, —CF$_3$, —OCF$_3$, —O—C$_{1-6}$ alkyl, and —C$_{1-6}$alkyl.

Embodiment 82 is the compound or salt of any one of the embodiments 75-81, wherein R$_C$ is selected from the group consisting of hydroxyl, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

Embodiment 83 is the compound or salt of any one of the embodiments 75-80, wherein R$_C$ is —C(O)OC$_{1-4}$ alkyl.

Embodiment 84 is the compound or salt of any one of the embodiments 75-80, wherein R$_C$ is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

Embodiment 85 is the compound or salt of any one of the embodiments 75-84, wherein W$_C$ is a covalent bond and X$_C$ is alkylene optionally interrupted by one or more —O— groups.

Embodiment 86 is the compound or salt of any one of the embodiments 75-85, wherein —W$_C$—X$_C$— is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—,
—CH$_2$CH$_2$CH$_2$CH$_2$CH$_2$CH$_2$—, or —CH$_2$CH$_2$—O—CH$_2$CH$_2$—.

Embodiment 87 is the compound or salt of any one of the embodiments 75-85, wherein —W$_C$—X$_C$— is —O—C$_{2-7}$alkylene- or —C$_{2-8}$alkylene-.

Embodiment 88 is the compound or salt of any of the embodiments 75-87, wherein Q$_C$ is a covalent bond or C$_{1-4}$alkylene.

Embodiment 89 is the compound or salt of any of the embodiments 75-88, wherein Q$_C$ is selected from the group consisting of a covalent bond, —CH$_2$—, —CH$_2$CH$_2$—, —CH$_2$CH$_2$CH$_2$—, and —CH$_2$CH$_2$CH$_2$CH$_2$—.

Embodiment 90 is the compound or salt of any of the embodiments 75-89, wherein Q$_C$ is selected from the group consisting of a covalent bond or —CH$_2$—.

Embodiment 91 is the compound or salt of any of the embodiments 75-90, wherein Q$_C$ is a covalent bond.

Embodiment 92 is the compound or salt of any of the embodiments 75-91, wherein R$_{8C}$ is selected from the group consisting of hydrogen, alkyl, and arylalkylenyl.

Embodiment 93 is the compound or salt of any of the embodiments 75-92, wherein R$_{8C}$ is hydrogen.

Embodiment 94 is the compound or salt of any one of the embodiments 75-93, wherein R$_{2C}$ is selected from the group consisting hydrogen, alkyl, alkoxyalkylenyl, alkylaminoalkylenyl, and hydroxyalkylenyl.

Embodiment 95 is the compound or salt of any one of the embodiments 75-94, wherein R$_{2C}$ is selected from the group consisting of hydrogen, alkyl, and alkoxyalkylenyl.

Embodiment 96 is the compound or salt of any one of the embodiments 75-95, wherein R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 97 is the compound or salt of any one of the embodiments 75-92, wherein R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, and —CH$_2$CH$_2$OH.

Embodiment 98 is the compound or salt of any one of the embodiments 75-92, wherein R$_{2C}$ is —CH$_2$NHOCH$_3$, —CH$_2$NHC(O)CH$_3$ or —CH$_2$NHC(O)cyclopropyl.

Embodiment 99 is the compound or salt of embodiments 75-84, wherein W$_C$ is selected from the group consisting of a covalent bond and —O—; X$_C$ is alkylene optionally interrupted by one or more —O— groups; t is 1; Q$_C$ is selected from the group consisting of a covalent bond or —CH$_2$—; R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 100 is the compound or salt of embodiments 75-80, wherein R$_{3C}$ and R$_{4C}$ are taken together to form a fused benzene ring that is unsubstituted; W$_C$ is selected from the group consisting of a covalent bond and —O—; X$_C$ is alkylene optionally interrupted by one or more —O— groups; Q$_C$ is a covalent bond; R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 101 is the compound or salt of embodiments 75-80, wherein R$_{3C}$ and R$_{4C}$ are taken together to form a fused benzene ring that is unsubstituted; W$_C$ is selected from the group consisting of a covalent bond and —O—; X$_C$ is alkylene optionally interrupted by one or more —O— groups; Q$_C$ is a covalent bond; R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$; R$_{8C}$ is selected from the group consisting of hydrogen and C$_{1-3}$alkyl.

Embodiment 102 is the compound or salt of any one of the embodiments 75-101, wherein the pharmaceutically acceptable salt is hydrochloride.

Embodiment 103 is the compound or salt of any one of the embodiments 75-101, wherein the pharmaceutically acceptable salt is dihydrochloride.

Embodiment 104 is a pharmaceutical composition comprising a therapeutically effective amount of a compound or salt of any one of the embodiments 75-103 in combination with a pharmaceutically acceptable carrier.

Embodiment 105 is a method of inducing cytokine biosynthesis in an animal comprising administering an effective amount of a compound or salt of any one of the embodiments 75-103 to the animal.

Embodiment 106 is a method of inducing biosynthesis of IFN-alpha in an animal comprising administering an effective amount of a compound or salt of any one of the embodiments 75-103 to the animal.

Embodiment 107 is a method of inducing biosynthesis of IFN-gamma in an animal comprising administering an effective amount of a compound or salt of any one of the embodiments 75-103 to the animal.

Embodiment 108 is a method of inducing biosynthesis of TNF-alpha in an animal comprising administering an effective amount of a compound or salt of any one of the embodiments 67-94 to the animal.

Embodiment 109 is a method of inducing biosynthesis of IP-10 in an animal comprising administering an effective amount of a compound or salt of any one of the embodiments 75-103 to the animal.

Embodiment 110 is a compound of Formula XXI:

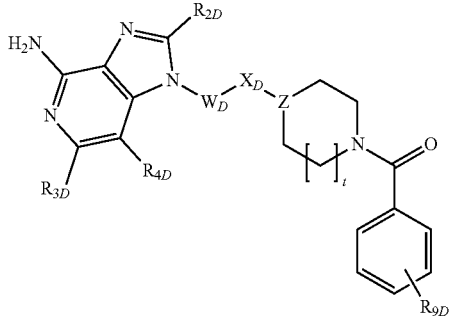

Formula XXI wherein:

R$_{3D}$ and R$_{4D}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R$_D$ groups.

R$_D$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$W_D$ is selected from the group consisting of a covalent bond, —O—, and —NH—;

$X_D$ is selected from the group consisting of alkylene, alkenylene, and alkynylene, wherein any of the alkylene, alkenylene, and alkynylene groups can be optionally interrupted by one or more —O— groups;

t is an integer from 0-4;

Z is —CH— or —N—;

$R_{9D}$ is -$Q_D$-N($R_{7D}$)—C(=N—$R_{5D}$)—N(H)$R_{6D}$;

$Q_D$ is selected from the group consisting of a covalent bond and alkylene;

$R_{2D}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{7D}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{5D}$ and $R_{6D}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 111 is the compound or salt of embodiment 110, wherein $R_{3D}$ and $R_{4D}$ are taken together to form a fused benzene ring or a fused pyridine ring; wherein the fused benzene ring or fused pyridine ring is either unsubstituted or substituted by one $R_D$ group.

Embodiment 112 is the compound or salt of embodiments 110-111, wherein $R_D$ is selected from the group consisting of halogen, hydroxyl, alkyl, alkoxy, and haloalkyl.

Embodiment 113 is the compound or salt of embodiment 110-112, t is l and Z is —CH—.

Embodiment 114 is the compound or salt of embodiment 110-113, wherein t is 1; Z is —CH—; and —$W_D$—$X_D$— is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$CH$_2$—, —CH$_2$CH$_2$—O—CH$_2$CH$_2$—O—CH$_2$CH$_2$—, —(CH$_2$)$_{2-4}$—O—(CH$_2$)$_{2-4}$—, —(CH$_2$)$_{2-4}$—(OCH$_2$CH$_2$—)$_{1-5}$, and —(CH$_2$)$_{2-6}$—(OCH$_2$C$_2$CH$_2$—)$_{1-4}$.

Embodiment 115 is the compound or salt of embodiment 110-114, wherein $R_{2D}$ is selected from the group consisting hydrogen, alkyl, and alkoxyalkylenyl.

Embodiment 116 is the compound or salt of embodiment 110-115, wherein $R_{2D}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 117 is the compound or salt of embodiment 110-116, wherein $Q_D$ is selected from the group consisting of a covalent bond and C$_{1-4}$alkylene.

Embodiment 118 is the compound or salt of embodiment 110-117, wherein $Q_D$ is selected from the group consisting of a covalent bond and —CH$_2$—.

Embodiment 119 is the compound or salt of embodiment 110-118, wherein $R_{7D}$ is hydrogen, C$_{1-8}$alkyl, or —CH$_2$Ph.

Embodiment 120 is the compound or salt of embodiment 110-119, wherein $R_{7D}$ is hydrogen or C$_{1-4}$alkyl.

Embodiment 121 is the compound or salt of embodiment 110-120, wherein $R_{7D}$ is hydrogen.

Embodiment 122 is the compound or salt of embodiment 110-121, wherein $R_{5D}$ and $R_{6D}$ are independently selected from the group consisting of hydrogen, alkyl, phenyl, and phenylalkylenyl.

Embodiment 123 is the compound or salt of embodiment 110-121, wherein $R_{5D}$ and $R_{6D}$ are independently selected from the group consisting of hydrogen, alkyl, cycloalkyl, cycloalkylalkylenyl, aryl, and arylalkylenyl.

Embodiment 124 is the compound or salt of embodiment 110-123, wherein $R_{5D}$ is hydrogen and $R_{6D}$ is hydrogen.

Embodiment 125 is the compound or salt of embodiment 110-124, $R_{5D}$ is hydrogen, $R_{6D}$ is hydrogen and $R_{7D}$ is hydrogen.

Embodiment 126 is the compound or salt of any one of the embodiments 110-125, wherein the pharmaceutically acceptable salt is hydrochloride.

Embodiment 127 is the compound or salt of any one of the embodiments 110-125, wherein the pharmaceutically acceptable salt is dihydrochloride.

Embodiment 128 is a pharmaceutical composition comprising a therapeutically effective amount of a compound or salt of any one of the embodiments 110-125 in combination with a pharmaceutically acceptable carrier.

Embodiment 129 is a method of inducing cytokine biosynthesis in an animal comprising administering an effective amount of a compound or salt of any one of the embodiments 110-125 to the animal.

Embodiment 130 is a method of inducing biosynthesis of IFN-alpha in an animal comprising administering an effective amount of a compound or salt of any one of the embodiments 110-125 to the animal.

Embodiment 131 is a method of inducing biosynthesis of IFN-gamma in an animal comprising administering an effective amount of a compound or salt of any one of the embodiments 110-125 to the animal.

Embodiment 132 is a method of inducing biosynthesis of TNF-alpha in an animal comprising administering an effective amount of a compound or salt of any one of the embodiments 110-125 to the animal.

Embodiment 133 is a method of inducing biosynthesis of IP-10 in an animal comprising administering an effective amount of a compound or salt of any one of the embodiments 110-125 to the animal.

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

EXAMPLES

Proton nuclear magnetic resonance ($^1$H NMR) analysis was conducted using an AVANCE III NMR spectrometer (Bruker Corporation, Bilerica, Mass.).

For Examples 2-5, the HPLC-MS analysis was conducted using an Agilent 1100 Series instrument with an Agilent 1100 Series Quadrupole detector and an Agilent Eclipse Plus C18 column (4.6 mm by 50 mm with a 3.5 micron particle diameter) (all obtained from Agilent Technologies, Santa Clara, Calif.). The mobile phase was a gradient of methanol to water/trifluoroacetic acid (0.1%) for ten minutes. The flow rate was 1.0 mL/minute and the products had retention times of 4.2-4.5 minutes.

Preparation of 4-[[[(Z)—N,N'-bis(tert-butoxycarbonyl)carbamimidoyl]amino]methyl]benzoic acid 4-(Aminomethyl)benzoic acid (2.15 g, obtained from Oakwood Products Incorporated, Estill, S.C.) was suspended in 10 mL of methanol. Triethylamine (10 mL) and N,N'-Bis-BOC-1-guanylpyrazole (4.50 g, obtained from Combi-Blocks Incorporated, San Diego, Calif.) were added and the reaction mixture stirred for 16 hours. Ammonium hydroxide (1 mL of a 23% aqueous solution) was added and the reaction mixture was stirred for 8 hours. Water (20 mL) and citric acid (150 mL of a 20% aqueous solution) were added and the reaction mixture was stirred for an additional 16 hours. A white precipitate formed which was isolated by filtration, rinsed with 50 mL of water, and dried under vacuum at 50° C. to provide 5.33 g of 4-[[[(Z)—N,N'-bis(tert-butoxycarbonyl)carbamimidoyl]amino]methyl]benzoic acid.

Preparation of 4-[[(Z)—N,N'-bis(tert-butoxycarbonyl)carbamimidoyl]amino]benzoic acid 4-Aminobenzoic acid (2.00 g, obtained from the Sigma-Aldrich Corporation, St. Louis, Mo.) was dissolved in 30 mL of methanol. N,N'-Bis-BOC-1-guanylpyrazole (4.50 g) was added and the reaction mixture heated to 60° C. for 4 hours. Upon cooling, a white precipitate formed which was isolated by filtration to provide 4.81 g of 4-[[(Z)—N,N'-bis(tert-butoxycarbonyl)carbamimidoyl]amino]benzoic acid.

Example 1

N-[4-(4-amino-2-propyl-imidazo[4,5-c]quinolin-1-yl)butyl]-4-guanidinobenzamide dihydrochloride

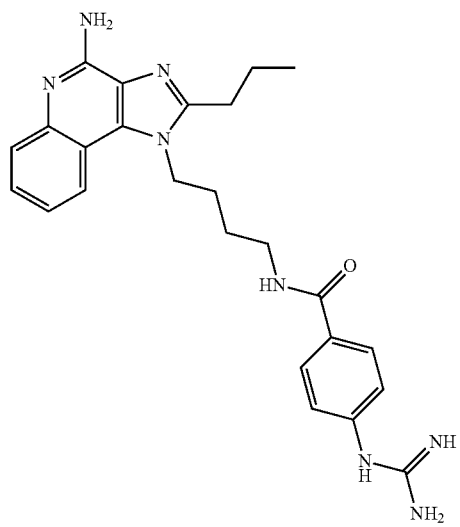 [SMILES: CCCc1nc2c(N)nc3ccccc3c2n1CCCCNC(=O)c1ccc(NC(=N)N)cc1]

A mixture of 4-guanidinobenzoic acid (5.0 g), N-hydroxysuccinimide (3.2 g), N,N-dimethylformamide (46 mL), and 1,3-dicyclohexylcarbodiimide (6.2 g) was stirred at room temperature for 16 hours and then filtered. The filtrate was concentrated under reduced pressure to provide (2,5-dioxopyrrolidin-1-yl)-4-guanidinobenzoate hydrochloride as a white solid.

1-(4-aminobutyl)-2-propyl-imidazo[4,5-c]quinolin-4-amine (0.5 g), 1,4-dioxane (16 mL), and (2,5-dioxopyrrolidin-1-yl)-4-guanidinobenzoate hydrochloride (0.63 g) were combined and then stirred at room temperature for 16 hours. The reaction was concentrated and then analyzed by HPLC-MS to confirm the preparation of N-[4-(4-amino-2-propyl-imidazo[4,5-c]quinolin-1-yl)butyl]-4-guanidinobenzamide dihydrochloride. MS m/z 459 (M+H)$^+$. The HPLC-MS analysis was conducted using an Agilent 1260 Infinity instrument with an Agilent 6130 Quadrupole detector and an Agilent Poroshell 120 EC-C18 column (4.6 mm by 50 mm with a 2.7 micron particle diameter) (all obtained from Agilent Technologies, Santa Clara, Calif.). The mobile phase was a gradient of water/ammonium acetate (0.1%) to acetonitrile (98%)/water/ammonium acetate (0.1%) for five minutes. The flow rate was 0.5 mL/minute and the product had a retention time of 3.3 minutes.

Example 2

N-[2-[2-(4-amino-2-butyl-imidazo[4,5-c]quinolin-1-yl)ethoxy]ethyl]-4-(guanidinomethyl)benzamide dihydrochloride

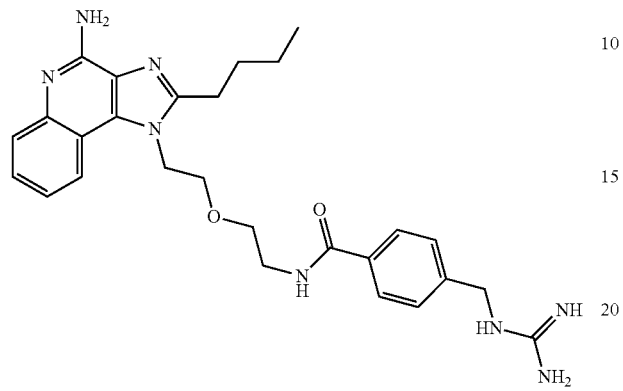

1-[2-(2-Aminoethoxy)ethyl]-2-butyl-imidazo[4,5-c]quinolin-4-amine (0.327 g) was dissolved in 20 mL of dichloromethane. Triethylamine (0.5 mL), 4-[[[(Z)—N,N'-bis(tert-butoxycarbonyl)carbamimidoyl]amino]methyl]benzoic acid (0.432 g), and benzotriazol-1-yloxy(tripyrrolidin-1-yl)phosphonium; hexafluorophosphate (PYBOP, 0.622 g obtained from Oakwood Products Incorporated) were then added and the reaction mixture was stirred for one hour. The reaction mixture was washed sequentially with 5 mL of 10% citric acid (aq) and 5 mL of 10% potassium carbonate (aq). The organic layer was then dried over magnesium sulfate, filtered and concentrated under reduced pressure. Purification by column chromatography [SiO$_2$, eluent of chloroform/(10% methanol/chloroform saturated with NH$_4$OH)] yielded tert-butyl (NZ)—N-[[[4-[2-[2-(4-amino-2-butyl-imidazo[4,5-c]quinolin-1-yl)ethoxy]ethylcarbamoyl]phenyl]methylamino]-(tert-butoxycarbonylamino)methylene]carbamate as a colorless oil that solidified on standing. The solid was dissolved in 5 mL of methanol and 5 mL of hydrochloric acid (12N) was added. The reaction mixture was stirred for 72 hours and then concentrated under reduced pressure. The resulting solid was recrystallized from methanol at 0° C. and isolated by filtration to provide 0.158 g of N-[2-[2-(4-amino-2-butyl-imidazo[4,5-c]quinolin-1-yl)ethoxy]ethyl]-4-(guanidinomethyl)benzamide dihydrochloride as a white powder. $^1$H NMR (DMSO, 300 MHz) 14.06 (s, 1H), 8.39 (t, J=6.3 Hz, 1H), 8.34-8.24 (m, 2H), 7.76 (d, J=8.3 Hz, 1H), 7.70-7.62 (m, 3H), 7.47 (t, J=8.3 Hz, 1H), 7.35 (d, J=8.3 Hz, 2H), 6.21 (b, 4H), 4.81 (m, 2H), 4.51 (d, J=6.3 Hz, 2H), 3.92 (m, 2H), 3.49 (m, 2H), 3.31 (m, 2H), 2.98 (t, J=7.5 Hz, 2H), 1.80 (m, 2H), 1.43 (m, 2H), 0.92 (t, J=7.3 Hz, 3H). MS m/z 503 (M+H)$^+$.

Example 3

N-[4-(4-amino-2-propyl-imidazo[4,5-c]quinolin-1-yl)butyl]-4-(guanidinomethyl)benzamide dihydrochloride

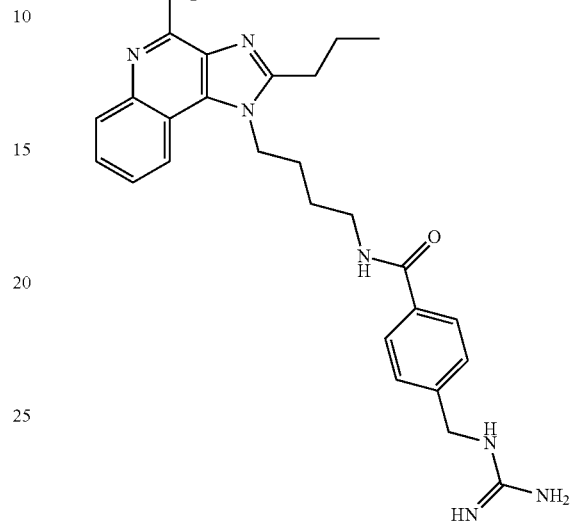

1-(4-Aminobutyl)-2-propyl-imidazo[4,5-c]quinolin-4-amine (0.297 g) was dissolved in 20 mL of dichloromethane. Triethylamine (0.5 mL), 4-[[[(Z)—N,N'-bis(tert-butoxycarbonyl)carbamimidoyl]amino]methyl]benzoic acid (0.430 g), and PYBOP (0.624 g) were then added and the reaction mixture was stirred for one hour. The reaction mixture was washed sequentially with 5 mL of 10% citric acid (aq) and 5 mL of 10% potassium carbonate (aq). The organic layer was then dried over magnesium sulfate, filtered and concentrated under reduced pressure. Purification by column chromatography [SiO$_2$, eluent of chloroform/(10% methanol/chloroform saturated with NH$_4$OH)] yielded tert-butyl (NZ)—N-[[[4-[4-(4-amino-2-propyl-imidazo[4,5-c]quinolin-1-yl)butylcarbamoyl]phenyl]methylamino]-(tert-butoxycarbonylamino)methylene]carbamate as a colorless oil that solidified on standing. The solid was dissolved in 5 mL of methanol and 5 mL of hydrochloric acid (12 N) was added. The reaction mixture was stirred for 72 hours and then concentrated under reduced pressure. The resulting solid was titurated with acetonitrile and isolated by filtration to provide 0.426 g of N-[4-(4-amino-2-propyl-imidazo[4,5-c]quinolin-1-yl)butyl]-4-(guanidinomethyl)benzamide dihydrochloride as a white powder. $^1$H NMR (DMSO, 300 MHz) 13.97 (s, 1H), 8.52 (t, J=5.5 Hz, 1H), 8.32 (t, J=6.3 Hz, 1H), 8.22 (d, J=8.2 Hz, 1H), 7.82-7.75 (m, 3H), 7.69 (t, J=7.3 Hz, 1H), 7.49 (t, J=7.2 Hz, 1H), 7.36 (d, J=8.3 Hz, 2H), 5.95 (b, 4H), 4.63 (t, J=7.4 Hz, 2H), 4.47 (d, J=6.2 Hz, 2H), 3.33 (q, J=5.9 Hz, 2H), 2.98 (t, J=7.4 Hz, 2H), 1.87 (m, 4H), 1.71 (m, 2H), 1.02 (t, J=7.3 Hz, 3H). MS m/z 473 (M+H)$^+$.

Example 4

N-[4-(4-amino-2-butyl-imidazo[4,5-c]quinolin-1-yl)butyl]-4-guanidinobenzamide dihydrochloride

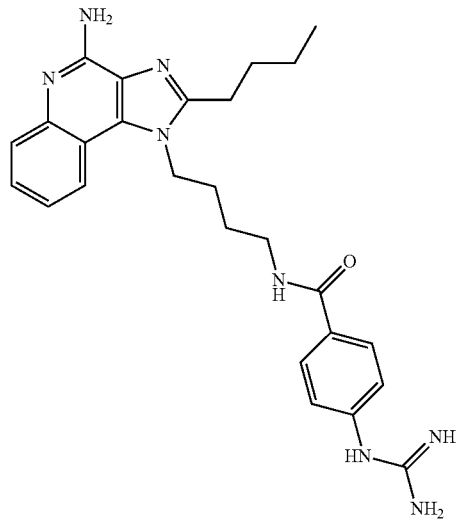 [SMILES: CCCCc1nc2c(N)nc3ccccc3c2n1CCCCNC(=O)c1ccc(NC(=N)N)cc1]

1-(4-Aminobutyl)-2-butyl-imidazo[4,5-c]quinolin-4-amine (0.312 g) was dissolved in 20 mL dichloromethane. Triethylamine (0.5 mL), 4-[[(Z)—N,N'-bis(tert-butoxycarbonyl)carbamimidoyl]amino]benzoic acid (0.418 g), and PYBOP (0.625 g) were then added and the reaction mixture was stirred for one hour. The reaction mixture was washed sequentially with 5 mL of 10% citric acid (aq) and 5 mL of 10% potassium carbonate (aq). The organic layer was then dried over magnesium sulfate, filtered and concentrated under reduced pressure. Purification by column chromatography [SiO$_2$, eluent of chloroform/(10% methanol/chloroform saturated with NH$_4$OH)] yielded tert-butyl (NZ)—N-[[4-[4-(4-amino-2-butyl-imidazo[4,5-c]quinolin-1-yl)butylcarbamoyl]anilino]-(tert-butoxycarbonylamino)methylene]carbamate, a colorless oil that solidified on standing. The solid was dissolved in 5 mL methanol and 5 mL of 12N Hydrochloric acid was added. The reaction mixture was stirred for 72 hours. The reaction mixture was then concentrated under reduced pressure and the resulting solid was recrystallized from a mixture of acetonitrile and methanol to provide 0.288 g of N-[4-(4-amino-2-butyl-imidazo[4,5-c]quinolin-1-yl)butyl]-4-guanidinobenzamide dihydrochloride as a white powder. $^1$H NMR (DMSO, 300 MHz) 14.11 (s, 1H), 10.44 (s, 1H), 8.60 (t, J=5.5 Hz, 1H), 8.32 (t, J=6.3 Hz, 1H), 8.23 (d, J=8.1 Hz, 1H), 7.85 (d, J=8.6 Hz, 2H), 7.82-7.67 (m, 6H), 7.52 (t, J=7.2 Hz, 1H), 7.29 (d, J=8.6 Hz, 2H), 4.63 (t, J=7.4 Hz, 2H), 3.34 (q, J=5.8 Hz, 2H), 2.99 (t, J=7.5 Hz, 2H), 1.93-1.65 (m, 6H), 1.51-1.39 (m, 2H), 0.94 (t, J=7.4 Hz, 3H). MS m/z 473 (M+H)$^+$.

Example 5

N-[4-(4-amino-2-butyl-imidazo[4,5-c]quinolin-1-yl)butyl]-4-(guanidinomethyl)benzamide dihydrochloride 1-(4-Aminobutyl)-2-butyl-imidazo[4,5-c]quinolin-4-amine (1.00 g) was dissolved in 50 mL of dichloromethane. Triethylamine (2.0 mL), 4-[[[(Z)—N,N'-bis(tert-butoxycarbonyl)carbamimidoyl]amino]methyl]benzoic acid (1.40 g), and PYBOP (2.0 g) were then added and the reaction mixture was stirred for 16 hours. The reaction mixture was washed sequentially with 5 mL of 10% citric acid (aq) and 5 mL of 10% potassium carbonate (aq). The organic layer was then dried over magnesium sulfate, filtered and concentrated under reduced pressure to obtain 3.42 g of a foam product. Purification by column chromatography [SiO$_2$, eluent of chloroform/(10% methanol/chloroform saturated with NH$_4$OH)] yielded 2.04 g of tert-butyl (NZ)—N-[[[4-[4-(4-amino-2-butyl-imidazo[4,5-c]quinolin-1-yl)butylcarbamoyl]phenyl]methylamino]-(tert-butoxycarbonylamino)methylene]carbamate as a light yellow oil that solidified on standing. Hydrochloric acid (aq) (12N, 10 mL) was then added and the reaction mixture was stirred for one hour. The reaction mixture was then concentrated under reduced pressure and the resulting solid was recrystallized from a mixture of acetonitrile and methanol to provide 1.36 g of N-[4-(4-amino-2-butyl-imidazo[4,5-c]quinolin-1-yl)butyl]-4-(guanidinomethyl)benzamide dihydrochloride as a white powder. $^1$H NMR (DMSO, 300 MHz) 14.07 (s, 1H), 8.53 (t, J=5.5 Hz, 1H), 8.38 (t, J=6.3 Hz, 1H), 8.19 (d, J=8.2 Hz, 1H), 7.83-7.73 (m, 3H), 7.69 (t, J=7.3 Hz, 1H), 7.49 (t, J=7.2 Hz, 1H), 7.36 (d, J=8.3 Hz, 2H), 5.36 (b, 2H), 4.63 (m, 2H), 4.48 (d, J=6.3 Hz, 2H), 3.31 (q, J=5.9 Hz, 2H), 2.99 (t, J=7.5 Hz, 2H), 1.95-1.64 (m, 6H), 1.45 (m, 2H), 0.93 (t, J=7.3 Hz, 3H). MS m/z 487 (M+H)$^+$.

Interferon-alpha (IFN-alpha), interferon-gamma (IFN-gamma) and tumor necrosis factor-alpha (TNF-alpha) cytokine levels (pg/mL) were measured using the procedure 'Cytokine Induction of Human Cells' described below. The only difference was that for Examples 2, 3, and 4 the diluted compounds were transferred to the PBMCs to achieve final compound concentrations of 100, 33.3, 11.1, 3.7, 1.23, and 0.41 micromolar. The positive control wells contained imiquimod serially diluted to concentrations of 100, 33.3, 11.1, 3.7, 1.23, and 0.41 micromolar. For Example 5, the diluted compound and positive control (imiquimod) were individually transferred to the PBMCs to achieve final concentrations of 30, 10, 3.3, 1.1, 0.37, 0.12, 0.04, and 0.01 micromolar. According to the procedure described below, IFN-alpha cytokine levels (pg/mL) were measured by using the ELISA assay (human IFN-α, pan specific, Mabtech, Cincinnati, Ohio). IFN-gamma and TNF-alpha levels (pg/mL) were measured by using the multiplex bead assay (magnetic beads, R & D Systems Minneapolis, Minn.) according to the manufacturer's instructions. The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 13.

TABLE 13

| Compound | MEC to Induce Cytokine (micromolar) | | |
| --- | --- | --- | --- |
|  | IFN-alpha | IFN-gamma | TNF-alpha |
| Example 2 | 1.2 | 1.2 | 3.7 |
| Example 3 | 3.7 | 3.7 | 3.7 |
| Example 4 | 0.4 | 3.7 | 1.2 |
| Example 5 | 0.37 | 1.1 | Not tested |

Cytokine Induction in Human Cells

Whole blood can be obtained from healthy human donors and collected by venipuncture into vacutainer tubes or syringes containing EDTA. Human peripheral blood mononuclear cells (PBMC) are purified from the whole blood by density gradient centrifugation. Histopaque 1077 (15 mL, Sigma, St. Louis, Mo.) is transferred to 6×50 mL sterile polypropylene conical tubes. The Histopaque is overlayed with 15-25 mL of blood diluted 1:2 in Hank's Balanced Salts Solution (HBSS) (Gibco, Life Technology, Grand Island N.Y.). The tubes are then centrifuged at 1370 rpm for 30 minutes at 20° C., with no brake (400×g, GH 3.8A Rotor).

The interface (buffy coat) containing the PBMC is collected and placed in a new sterile 50 mL conical polypropylene centrifuge tube. The PBMC are mixed with an equal volume of HBSS about 20 mL from the interface and about 20 mL of HBSS), and then centrifuged at 1090 rpm, 10 min, 20° C., with brake (270×g, GH 3.8A Rotor). After completing centrifugation, the cells are resuspended in 2-3 mL ACK Red blood cell lysis buffer (ammonium chloride potassium solution, Gibco, Life Technology) and incubated for 2-5 minutes at 20° C. Next, HBSS (40 mL) is added to the cells, and the sample is centrifuged at 270×g for 10 min at 20° C. The supernatant is decanted, and the cell pellet is resuspended in 5 mL AIM V® Medium (Gibco, Life Technology). Cell aggregates and debris are removed by filtering the cell solution through a BD Falcon 70 micron nylon cell strainer (BD Biosciences, San Jose, Calif.).

The number of viable cells is determined by counting with a Miltenyi FACS instrument (Miltenyi Biotec Inc., San Diego, Calif.) or by using a hemacytometer. For determining cell viability with a hemacytometer, the cells are diluted 1/10 in 0.4% trypan blue and HBSS (specifically, 50 microliter of trypan blue+40 microliter of HBSS+10 microliter of cell solution are added to a microfuge tube and mixed). Ten microliters of the diluted cells are then applied to the hemacytometer, and the number of viable PBMC are determined by microscopy.

The PBMC sample is then resuspended in 96-well plates at a concentration of 8×10$^5$ cells/well in 0.1 mL of AIM-V medium. Each compound is solubilized in DMSO to create a 3 mM stock solution. The stock solution is then further diluted with AIM-V medium to prepare the serial dilutions. The diluted compound (100 microliters) is then transferred to the PBMCs to achieve final compound concentrations of 10, 1, 0.1, 0.01, 0.001, 0.0001 micromolar. The plates also have both positive and negative controls. The negative control wells contain only AIM-V medium with no example compound. The positive control wells contain imiquimod serially diluted to concentrations of 10, 1, 0.1, 0.01, 0.001, 0.0001 micromolar. The plates are then cultured at 37'C/5% $CO_2$ for 21-24 hrs. Cell-free supernatants are harvested by centrifuging the 96-well plates at 2100 rpm, 23° C. for 10 minutes. Approximately 160 microliter of the supernatant is then stored in a NUNC 96-well plate, covered with the compression cap and stored at −80° C. until the cytokine analysis is done.

IFN-alpha cytokine levels (pg/mL) can be measured by ELISA (human IFN-α, pan specific, Mabtech, Cincinnati, Ohio). IFN-gamma, TNF-alpha, and IP-10 cytokine levels (pg/mL) can be measured by multiplex bead assay (magnetic beads, R & D Systems Minneapolis, Minn.) according to the manufacturer's instructions.

The data can be analyzed to determine the minimum effective concentration (MEC) for each compound at which induction of a particular cytokine is observed in the assay. Specifically, the minimum effective concentration of each compound (micromolar) can be determined as the lowest concentration of the compound that induced a measured cytokine response at a level (pictograms/mL) that is at least 2× greater than that observed with the negative control wells.

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A compound of the Formula (I):

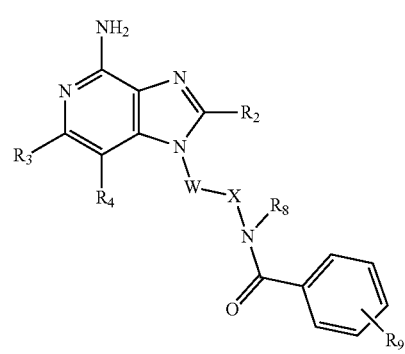

Formula I wherein:
R₃ and R₄ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;

R is selected from the group consisting of halogen, hydroxyl, alkyl, alkoxy, haloalkyl, —C(O)—O-alkyl, —C(O)—O—CH₂Ph, —C(O)—O-aryl, amino, alkylamino, and dialkylamino aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroaryalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

W is selected from the group consisting of a covalent bond, —O—, and NH—;

X is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

R₉ is -Q-N(R₇)—C(═N—R₅)—N(H)R₆;

Q is selected from the group consisting of a covalent bond and alkylene;

R₂ is selected from the group consisting of hydrogen, alkyl, alkenyl, alkynyl, —O-alkyl, hydroxyalkylenyl, alkoxyalkylenyl, alkylaminoalkylenyl, hydroxyl, —CH₂—NH—O-alkyl, and —CH₂NHC(O)-alkyl;

R₈ is selected from the group consisting of hydrogen, alkyl, arylalkylenyl, alkoxyalkylenyl, aryloxyalkylenyl, benzyloxyalkylenyl, aryl-(CH₂)₂₋₆—O-alkylenyl, and cycloalkylalkylenyl; wherein any of the alkyl, arylalkylenyl, alkoxyalkylenyl, aryloxyalkylenyl, benzyloxyalkylenyl, aryl-(CH₂)₂₋₆—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

R₇ is selected from the group consisting of hydrogen, alkyl, arylalkylenyl, alkoxyalkylenyl, aryloxyalkylenyl, benzyloxyalkylenyl, aryl-(CH₂)₂₋₆—O-alkylenyl, and cycloalkylalkylenyl; wherein any of the alkyl, arylalkylenyl, alkoxyalkylenyl, aryloxyalkylenyl, benzyloxyalkylenyl, aryl-(CH₂)₂₋₆—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

R₅ and R₆ are independently selected from the group consisting of hydrogen, —C(O)—O— alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH₂)₂₋₆—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH₂)₂₋₆—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; or a pharmaceutically acceptable salt thereof.

2. The compound or salt of claim 1, wherein R₃ and R₄ are taken together to form a fused benzene ring, a fused pyridine ring, or a fused cyclohexene ring, and the fused benzene ring, fused pyridine ring, or fused cyclohexene ring is either unsubstituted or substituted by one and only one R group.

3. The compound or salt of claim 1, wherein R₇ is hydrogen and R₈ is hydrogen.

4. The compound or salt of claim 1, wherein W is a covalent bond or —O—.

5. The compound or salt of claim 1, wherein X is alkylene optionally interrupted by one or more —O— groups.

6. The compound or salt of claim 1, wherein X is selected from the group consisting of —CH₂CH₂—, —CH₂CH₂CH₂—, —CH₂CH₂CH₂CH₂—, —CH₂CH₂CH₂CH₂CH₂—, —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂C(CH₃)₂—, —CH₂C(CH₃)₂CH₂—, —CH₂CH₂—O—CH₂CH₂—, —CH₂CH₂—O—CH₂CH₂CH₂—, —CH₂CH₂—O—CH₂CH₂—O—CH₂CH₂—, —(CH₂)₂₋₄—O—(CH₂)₂₋₄—, —(CH₂)₂₋₄—(OCH₂CH₂-)₁₋₅, and —(CH₂)₂₋₆—(OCH₂CH₂-)₁₋₄.

7. The compound or salt of claim 1, wherein X is —C₁₋₅alkylene-arylene-C₁₋₅alkylene- or —C₁₋₅alkylene-heteroarylene-C₁₋₅alkylene-.

8. The compound or salt of claim 1, wherein X is —CH₂-phenylene-CH₂—.

9. The compound or salt of claim 1, wherein R₂ is selected from the group consisting hydrogen, alkyl, alkoxyalkylenyl.

10. The compound or salt of claim 1, wherein R₂ is selected from the group consisting of hydrogen, —CH₃, —CH₂CH₃, —CH₂CH₂CH₃, —CH₂CH₂CH₂CH₃, —CH₂OCH₃, —CH₂OCH₂CH₃, —CH₂CH₂OCH₃.

11. The compound or salt of claim 1, wherein R₅ and R₆ are independently selected from the group consisting of hydrogen, alkyl, phenyl, and phenylalkylenyl.

12. The compound or salt of claim 1, wherein R₅ is hydrogen and R₆ is hydrogen.

13. A compound of the Formula XIV:

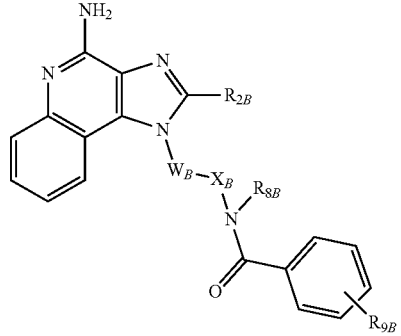

Formula XIV wherein:
W_B is selected from the group consisting of a covalent bond, —O—, and —NH—;
X_B is selected from the group consisting of alkylene, alkenylene, and alkynylene, wherein any of the alkylene, alkenylene, and alkynylene groups can be optionally interrupted or terminated by arylene or heteroarylene and optionally interrupted by one or more —O— groups;

$R_{9B}$ is -$Q_B$-N($R_{7B}$)—C(=N—$R_{5B}$)—N(H)$R_{6B}$;

$Q_B$ is selected from the group consisting of a covalent bond and alkylene;

$R_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2$NHC(O)-alkyl;

$R_{8B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{7B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{5B}$ and $R_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl;

wherein any of the, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino;

or a pharmaceutically acceptable salt thereof.

14. The compound or salt of claim 13, wherein $R_{7B}$ is hydrogen and $R_{8B}$ is hydrogen.

15. The compound or salt of claim 13, wherein $R_{2B}$ is selected from the group consisting hydrogen, alkyl, alkoxyalkylenyl.

16. The compound or salt of claim 13, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

17. The compound or salt of claim 13, wherein $R_{5B}$ and $R_{6B}$ are independently selected from the group consisting of hydrogen, alkyl, phenyl, phenylalkylenyl.

18. The compound or salt of claim 13, wherein $R_{5B}$ is hydrogen and $R_{6B}$ is hydrogen.

19. The compound or salt of claim 13, wherein $X_B$ is alkylene optionally interrupted by one or more —O— groups.

20. The compound or salt of claim 13, wherein $X_B$ is selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2$—, —$CH_2CH_2$—O—$CH_2CH_2$—O—$CH_2CH_2$—, —$(CH_2)_{2-4}$—O—$(CH_2)_{2-4}$—, —$(CH_2)_{2-4}$—(OCH$_2$CH$_2$-)$_{1-5}$, and —$(CH_2)_{2-6}$—(OCH$_2$CH$_2$-)$_{1-4}$.

21. The compound or salt of claim 13, wherein $X_B$ is —$C_{1-5}$alkylene-arylene-$C_{1-5}$alkylene- or —$C_{1-5}$alkylene-heteroarylene-$C_{1-5}$alkylene-.

22. The compound or salt of claim 13, wherein $X_B$ is —$CH_2$-phenylene-$CH_2$—.

23. A method of inducing biosynthesis of IFN-alpha in an animal comprising administering an effective amount of a compound or salt of claim 1 to the animal.

24. A pharmaceutical composition comprising a therapeutically effective amount of a compound or salt of claim 1 in combination with a pharmaceutically acceptable carrier.

\* \* \* \* \*